(12) United States Patent
Plambeck et al.

(10) Patent No.: US 9,345,569 B2
(45) Date of Patent: May 24, 2016

(54) CORNEAL IMPLANT STORAGE AND DELIVERY DEVICES

(71) Applicant: REVISION OPTICS, INC., Lake Forest, CA (US)

(72) Inventors: Gregg Edmond Plambeck, Aliso Viejo, CA (US); Ned Schneider, Aliso Viejo, CA (US); Adam Ariely, Lake Forest, CA (US); David Matsuura, Encinitas, CA (US); Philip Simpson, Encinitas, CA (US)

(73) Assignee: REVISION OPTICS, INC., Lake Forest, CA (US)

( * ) Notice: Subject to any disclaimer, the term of this patent is extended or adjusted under 35 U.S.C. 154(b) by 215 days.

(21) Appl. No.: 14/352,628

(22) PCT Filed: Oct. 22, 2012

(86) PCT No.: PCT/US2012/061366
§ 371 (c)(1),
(2) Date: Apr. 17, 2014

(87) PCT Pub. No.: WO2013/059813
PCT Pub. Date: Apr. 25, 2013

(65) Prior Publication Data
US 2014/0257477 A1    Sep. 11, 2014

Related U.S. Application Data

(60) Provisional application No. 61/550,185, filed on Oct. 21, 2011, provisional application No. 61/606,674, filed on Mar. 5, 2012, provisional application No. 61/679,482, filed on Aug. 3, 2012.

(51) Int. Cl.
*A61F 2/14* (2006.01)
*A61F 2/00* (2006.01)
*A61B 19/02* (2006.01)

(52) U.S. Cl.
CPC ............ *A61F 2/143* (2013.01); *A61B 19/0271* (2013.01); *A61F 2/0095* (2013.01); *A61F 2/142* (2013.01); *A61F 2/148* (2013.01); *A61B 19/0256* (2013.01); *A61F 2/1451* (2015.04)

(58) Field of Classification Search
CPC . G02B 1/043; A61F 2/14; A61F 2009/00872; A61F 2009/00897; A61F 9/008; A61F 9/00827; A61F 9/00836; A61F 2/148; A61L 27/16; A61L 2430/16; C08L 83/04
USPC ........................................................ 606/107
See application file for complete search history.

(56) References Cited

U.S. PATENT DOCUMENTS

| | | |
|---|---|---|
| 2,521,161 A | 9/1950 | Grover |
| 2,714,721 A | 8/1955 | Stone, Jr. |

(Continued)

FOREIGN PATENT DOCUMENTS

| | | |
|---|---|---|
| DE | 3208729 A1 | 9/1983 |
| EP | 0308077 A2 | 3/1989 |

(Continued)

OTHER PUBLICATIONS

Patel et al.; Refractive index of human corneal epithelium and stroma; J. Refract. Surg.; 11(2); Abstract; Mar. 1995 (pubmed Abstract only).

(Continued)

*Primary Examiner* — David H Willse
*Assistant Examiner* — Tiffany Shipmon
(74) *Attorney, Agent, or Firm* — Shay Glenn LLP

(57) ABSTRACT

Devices and methods for handling and depositing corneal implants onto corneal tissue. Devices and methods for packaging and storing corneal implants.

13 Claims, 44 Drawing Sheets

(56) References Cited

U.S. PATENT DOCUMENTS

| | | |
|---|---|---|
| 3,091,328 A | 5/1963 | Leonardos |
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |
| 3,996,627 A | 12/1976 | Deeg et al. |
| 4,030,480 A | 6/1977 | Meyer |
| 4,037,604 A | 7/1977 | Newkirk |
| 4,039,827 A | 8/1977 | Zdrok et al. |
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,573,998 A | 3/1986 | Mazzocco |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,912 A | 6/1992 | Kaplan et al. |
| 5,123,921 A | 6/1992 | Werblin et al. |
| 5,139,518 A | 8/1992 | White |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,352,233 A | 10/1994 | Anis |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,487,377 A | 1/1996 | Smith et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |

(56) References Cited

U.S. PATENT DOCUMENTS

| | | | |
|---|---|---|---|
| 5,570,142 A | 10/1996 | Lieberman |
| 5,591,185 A | 1/1997 | Kilmer et al. |
| 5,598,234 A | 1/1997 | Blum et al. |
| 5,601,584 A | 2/1997 | Obagi et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,657,108 A | 8/1997 | Portney |
| 5,682,223 A | 10/1997 | Menezes et al. |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,728,155 A | 3/1998 | Anello et al. |
| 5,732,990 A | 3/1998 | Yavitz et al. |
| 5,752,928 A | 5/1998 | de Roulhac et al. |
| 5,755,785 A | 5/1998 | Rowsey et al. |
| 5,766,181 A | 6/1998 | Chambers et al. |
| 5,772,667 A | 6/1998 | Blake |
| 5,779,711 A | 7/1998 | Kritzinger et al. |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,873,889 A | 2/1999 | Chin |
| 5,876,439 A | 3/1999 | Lee |
| 5,888,243 A | 3/1999 | Silverstrini |
| 5,913,898 A | 6/1999 | Feingold |
| 5,919,185 A | 7/1999 | Peyman |
| 5,928,245 A | 7/1999 | Wolf et al. |
| 5,929,968 A | 7/1999 | Cotie et al. |
| 5,929,969 A | 7/1999 | Roffman |
| 5,935,140 A | 8/1999 | Buratto |
| 5,941,583 A | 8/1999 | Raimondi |
| 5,944,752 A | 8/1999 | Silvestrini |
| 5,945,498 A | 8/1999 | Hopken et al. |
| 5,964,748 A | 10/1999 | Peyman |
| 5,964,776 A | 10/1999 | Peyman |
| 5,968,065 A | 10/1999 | Chin |
| 5,976,150 A | 11/1999 | Copeland |
| 5,976,168 A | 11/1999 | Chin |
| 5,980,549 A | 11/1999 | Chin |
| 6,007,510 A | 12/1999 | Nigam |
| 6,010,510 A | 1/2000 | Brown et al. |
| 6,024,448 A | 2/2000 | Wu et al. |
| 6,033,395 A | 3/2000 | Peyman |
| 6,036,714 A | 3/2000 | Chin |
| 6,050,999 A | 4/2000 | Paraschac et al. |
| 6,055,990 A | 5/2000 | Thompson |
| 6,066,170 A | 5/2000 | Lee |
| 6,068,642 A | 5/2000 | Johnson et al. |
| 6,079,826 A | 6/2000 | Appleton et al. |
| 6,083,231 A | 7/2000 | Van Noy et al. |
| 6,086,202 A | 7/2000 | Chateau et al. |
| 6,090,141 A | 7/2000 | Lindstrom |
| 6,102,946 A | 8/2000 | Nigam |
| 6,110,166 A | 8/2000 | Juhasz |
| 6,120,148 A | 9/2000 | Fiala et al. |
| 6,125,294 A | 9/2000 | Scholl et al. |
| 6,129,733 A | 10/2000 | Brady et al. |
| 6,139,560 A | 10/2000 | Kremer |
| 6,142,969 A | 11/2000 | Nigam |
| 6,143,001 A | 11/2000 | Brown et al. |
| 6,159,241 A | 12/2000 | Lee et al. |
| 6,171,324 B1 | 1/2001 | Cote et al. |
| 6,175,754 B1 | 1/2001 | Scholl et al. |
| RE37,071 E | 2/2001 | Gabrielian et al. |
| 6,183,513 B1 | 2/2001 | Guenthner et al. |
| 6,197,019 B1 | 3/2001 | Peyman |
| 6,197,057 B1 | 3/2001 | Peyman et al. |
| 6,197,058 B1 | 3/2001 | Portney |
| 6,203,538 B1 | 3/2001 | Peyman |
| 6,203,549 B1 | 3/2001 | Waldock |
| 6,203,557 B1 | 3/2001 | Chin |
| 6,206,919 B1 | 3/2001 | Lee |
| 6,210,005 B1 | 4/2001 | Portney |
| 6,214,015 B1 | 4/2001 | Reich et al. |
| 6,214,044 B1 | 4/2001 | Silverstrini |
| 6,217,571 B1 | 4/2001 | Peyman |
| 6,221,067 B1 | 4/2001 | Peyman |
| 6,228,113 B1 | 5/2001 | Kaufman |
| 6,228,114 B1 | 5/2001 | Lee |
| 6,248,111 B1 | 6/2001 | Glick et al. |
| 6,250,757 B1 | 6/2001 | Roffman et al. |
| 6,251,114 B1 | 6/2001 | Farmer et al. |
| 6,264,648 B1 | 7/2001 | Peyman |
| 6,264,670 B1 | 7/2001 | Chin |
| 6,264,692 B1 | 7/2001 | Woffinden et al. |
| 6,267,768 B1 | 7/2001 | Deacon et al. |
| 6,271,281 B1 | 8/2001 | Liao et al. |
| 6,277,137 B1 | 8/2001 | Chin |
| 6,280,449 B1 | 8/2001 | Blake |
| 6,280,470 B1 | 8/2001 | Peyman |
| 6,283,595 B1 | 9/2001 | Breger |
| 6,302,877 B1 | 10/2001 | Ruiz |
| 6,325,509 B1 | 12/2001 | Hodur et al. |
| 6,325,792 B1 | 12/2001 | Swinger et al. |
| 6,350,272 B1 | 2/2002 | Kawesch |
| 6,361,560 B1 | 3/2002 | Nigam |
| 6,364,483 B1 | 4/2002 | Grossinger et al. |
| 6,371,960 B2 | 4/2002 | Heyman et al. |
| 6,391,230 B1 | 5/2002 | Sarbadhikari |
| 6,398,277 B1 | 6/2002 | McDonald |
| 6,398,789 B1 | 6/2002 | Capetan |
| 6,428,572 B2 | 8/2002 | Nagai |
| 6,435,681 B2 | 8/2002 | Portney |
| 6,436,092 B1 | 8/2002 | Peyman |
| 6,447,519 B1 | 9/2002 | Brady et al. |
| 6,447,520 B1 | 9/2002 | Ott et al. |
| 6,458,141 B1 | 10/2002 | Peyman |
| 6,461,384 B1 | 10/2002 | Hoffmann et al. |
| 6,471,708 B2 | 10/2002 | Green |
| 6,474,814 B1 | 11/2002 | Griffin |
| 6,506,200 B1 | 1/2003 | Chin |
| 6,511,178 B1 | 1/2003 | Roffman et al. |
| 6,527,389 B2 | 3/2003 | Portney |
| 6,537,283 B2 | 3/2003 | Van Noy |
| 6,543,610 B1 | 4/2003 | Nigam |
| 6,544,286 B1 | 4/2003 | Perez |
| 6,551,307 B2 | 4/2003 | Peyman |
| 6,554,424 B1 | 4/2003 | Miller et al. |
| 6,554,425 B1 | 4/2003 | Roffman et al. |
| 6,557,998 B2 | 5/2003 | Portney |
| 6,581,993 B2 | 6/2003 | Nigam |
| 6,582,076 B1 | 6/2003 | Roffman et al. |
| 6,589,057 B1 | 7/2003 | Keenan et al. |
| 6,589,203 B1 | 7/2003 | Mitrev |
| 6,589,280 B1 | 7/2003 | Koziol |
| 6,592,591 B2 | 7/2003 | Polla et al. |
| 6,596,000 B2 | 7/2003 | Chan et al. |
| 6,605,093 B1 | 8/2003 | Blake |
| 6,607,537 B1 | 8/2003 | Binder |
| 6,607,556 B1 | 8/2003 | Nigam |
| 6,623,522 B2 | 9/2003 | Nigam |
| 6,626,941 B2 | 9/2003 | Nigam |
| 6,629,979 B1 | 10/2003 | Feingold et al. |
| 6,632,244 B1 | 10/2003 | Nigam |
| 6,641,577 B2 | 11/2003 | Bille |
| 6,645,246 B1 | 11/2003 | Weinschenk, III et al. |
| 6,648,877 B1 | 11/2003 | Juhasz et al. |
| 6,657,029 B2 | 12/2003 | Vanderbilt |
| 6,666,887 B1 | 12/2003 | Callahan et al. |
| 6,673,112 B2 | 1/2004 | Nigam |

(56) References Cited

U.S. PATENT DOCUMENTS

| | | |
|---|---|---|
| 6,702,807 B2 | 3/2004 | Peyman |
| 6,709,103 B1 | 3/2004 | Roffman et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,733,526 B2 | 5/2004 | Paul et al. |
| 6,808,262 B2 | 10/2004 | Chapoy et al. |
| 6,824,178 B2 | 11/2004 | Nigam |
| 6,849,090 B2 | 2/2005 | Nigam |
| 6,855,163 B2 | 2/2005 | Peyman |
| 6,875,232 B2 | 4/2005 | Nigam |
| 6,879,402 B2 | 4/2005 | Küchel |
| 6,881,197 B1 | 4/2005 | Nigam |
| 6,893,461 B2 | 5/2005 | Nigam |
| 6,949,093 B1 | 9/2005 | Peyman |
| 6,955,432 B2 | 10/2005 | Graham |
| 7,128,351 B2 | 10/2006 | Nigam |
| 7,585,075 B2 | 9/2009 | Marmo |
| 7,699,837 B2 | 4/2010 | Cox et al. |
| 7,776,086 B2 | 8/2010 | Miller |
| 7,976,577 B2 | 7/2011 | Silvestrini |
| 7,992,906 B2 | 8/2011 | Nigam |
| 8,057,541 B2 | 11/2011 | Dishler et al. |
| 8,162,953 B2 | 4/2012 | Dishler et al. |
| 8,469,948 B2 | 6/2013 | Dishler et al. |
| 8,540,727 B2 | 9/2013 | Dishler et al. |
| 8,668,735 B2 | 3/2014 | Nigam et al. |
| 8,685,292 B2 | 4/2014 | Mandler et al. |
| 2001/0027314 A1 | 10/2001 | Peyman |
| 2001/0051826 A1 | 12/2001 | Bogaert et al. |
| 2002/0010510 A1 | 1/2002 | Silvestrini |
| 2002/0055753 A1 | 5/2002 | Silvestrini |
| 2002/0101563 A1 | 8/2002 | Miyamura et al. |
| 2002/0103538 A1 | 8/2002 | Hughes et al. |
| 2002/0138069 A1 | 9/2002 | Peyman |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0208190 A1 | 11/2003 | Roberts et al. |
| 2003/0220653 A1 | 11/2003 | Perez |
| 2003/0229303 A1 | 12/2003 | Haffner et al. |
| 2004/0010278 A1 | 1/2004 | Nakamura et al. |
| 2004/0019379 A1 | 1/2004 | Glick et al. |
| 2004/0034413 A1 | 2/2004 | Christensen |
| 2004/0054408 A1 | 3/2004 | Glick et al. |
| 2004/0073303 A1 | 4/2004 | Schanzlin |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0182488 A1 | 8/2005 | Peyman |
| 2005/0203494 A1 | 9/2005 | Holliday |
| 2005/0222679 A1 | 10/2005 | Peyman |
| 2005/0246016 A1 | 11/2005 | Miller et al. |
| 2006/0004381 A1 | 1/2006 | Feingold et al. |
| 2006/0020267 A1 | 1/2006 | Marmo |
| 2006/0116762 A1 | 6/2006 | Hong et al. |
| 2006/0134170 A1 | 6/2006 | Griffith et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0038276 A1 | 2/2007 | Yaldo |
| 2007/0106318 A1 | 5/2007 | McDonald |
| 2007/0106376 A1 | 5/2007 | Roberts et al. |
| 2007/0129797 A1 | 6/2007 | Lang et al. |
| 2007/0182920 A1 | 8/2007 | Back et al. |
| 2007/0244559 A1 | 10/2007 | Shiuey |
| 2007/0255401 A1 | 11/2007 | Lang |
| 2007/0280994 A1 | 12/2007 | Cunanan |
| 2008/0262610 A1 | 10/2008 | Lang et al. |
| 2008/0269771 A1 | 10/2008 | Fulcher |
| 2008/0281304 A1 | 11/2008 | Campbell |
| 2009/0079940 A1 | 3/2009 | Dai et al. |
| 2009/0198325 A1 | 8/2009 | Holliday et al. |
| 2009/0216217 A1 | 8/2009 | Odrich et al. |
| 2009/0326650 A1 | 12/2009 | Zickler et al. |
| 2010/0241060 A1 | 9/2010 | Roizman et al. |
| 2010/0331831 A1 | 12/2010 | Bischoff et al. |
| 2011/0149241 A1 | 6/2011 | Dai |
| 2011/0208300 A1 | 8/2011 | de Juan et al. |
| 2011/0218623 A1 | 9/2011 | Dishler et al. |
| 2011/0256806 A1 | 10/2011 | Monnoyeur |
| 2011/0290681 A1 | 12/2011 | Nigam |
| 2012/0203238 A1 | 8/2012 | Nigam |
| 2012/0231416 A1 | 9/2012 | Drapeau et al. |
| 2012/0238806 A1 | 9/2012 | Mangiardi et al. |
| 2012/0245592 A1 | 9/2012 | Berner et al. |
| 2013/0023892 A1 | 1/2013 | Schneider et al. |
| 2013/0060255 A1 | 3/2013 | Feingold et al. |
| 2013/0211523 A1 | 8/2013 | Southard et al. |
| 2013/0231739 A1 | 9/2013 | Dishler et al. |
| 2013/0253527 A1 | 9/2013 | Schneider et al. |
| 2013/0253529 A1 | 9/2013 | Walter et al. |
| 2013/0281993 A1 | 10/2013 | Dishler et al. |
| 2013/0317605 A1 | 11/2013 | Ide et al. |
| 2013/0324983 A1 | 12/2013 | Liang |
| 2014/0135915 A1 | 5/2014 | Nigam et al. |
| 2014/0288540 A1 | 9/2014 | Bischoff et al. |
| 2015/0080865 A1 | 3/2015 | Holliday et al. |

FOREIGN PATENT DOCUMENTS

| | | |
|---|---|---|
| EP | 0420549 A2 | 4/1991 |
| EP | 0729323 B1 | 7/1998 |
| EP | 0668061 B1 | 9/2000 |
| JP | S5973622 A | 4/1984 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2002537895 | 11/2002 |
| JP | 03-508135 | 3/2003 |
| JP | 2007500070 | 1/2007 |
| WO | WO92/08423 A1 | 5/1992 |
| WO | WO93/05731 A1 | 4/1993 |
| WO | WO96/26690 A1 | 9/1996 |
| WO | WO98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO 2005/107648 A2 | 11/2005 |
| WO | WO 2006/029316 A1 | 4/2006 |
| WO | WO 2006/060363 A2 | 6/2006 |
| WO | WO 2007/101016 A2 | 9/2007 |
| WO | WO 2007/132332 A2 | 11/2007 |

OTHER PUBLICATIONS

Esguerra et al.; U.S. Appl. No. 14/463,355 entitled "Corneal implant storage, packaging, and delivery devices,", filed Aug. 19, 2014.

Winn et al.; Factors affecting light-adapted pupil size in normal human subjects; Investigative Ophthalmology and Visual Science; 35(3); pp. 1132-1137; Mar. 1994.

Collins et al.; U.S. Appl. No. 14/575,833 entitled "Integrated part fixturing for lathing processes,", filed Dec. 18, 2014.

(56) References Cited

OTHER PUBLICATIONS

Dymax; UV curable optical assembly; 2 pages; retrieved Mar. 4, 2015 from the internet (http:www.dymax.com/index.php/adhesives/optical).

Sharma et al.; U.S. Appl. No. 14/211,714 entitled "Pre-treatment haze reduction for corneal inlays,", filed Mar. 14, 2014.

Long et al.; U.S. Appl. No. 14/217,056 entitled "Anterior corneal shapes and methods of providing the shapes,", filed Mar. 17, 2014.

Alio, J. J., et al., "Intracorneal Inlay Complicated by Intrastomal Epithelial Opacification," Arch Ophthalmol, Oct. 2004; vol. 122; 6 pages.

Cheng, et al.; "Predicting subjective judgment of best focus with objective image quality metrics"; Journal of Vision; Apr. 23, 2004; vol. 4(4); pp. 310-321.

Churms, P.W., "The Theory and Computation of Optical Modifications to the Cornea in Refractive Keratoplasty," American Journal of Optometry & Physiological Optics, 56:2, pp. 67-74, Feb. 1979.

Huang et al.; Mathematical Model of Corneal Surface Smoothing After Laser Refractive Surgery; American Journal of Ophthalmology; Mar. 2003; pp. 267-278.

Lang, A.J. et al., "First order design of intracorneal inlays: dependence on keratometric flap and corneal properties," ARVO Abstracts 2006, poster No. 3591, May 3, 2006.

Liou, H. L. et al., "Anatomically accurate, finite model eye for optical modeling", Journal of the Optical Society of America, vol. 14, No. 8, Aug. 1997.

Marsack, et al.; "Metrics of optical quality derived from wave aberrations predict visual performance"; Journal of Vision; Apr. 23, 2004; vol. 4(4); pp. 322-328.

Navarro et al.; Accommodation-dependent model of the human eye with aspherics; J. Opt. Soc Am. A; vol. 2; No. 8; Aug. 1985; pp. 1273-1281.

Watsky, M.A. et al., "Predicting Refractive Alterations with Hydrogel Keratophakia," Investigative Opthalmology & Visual Science, vol. 26, pp. 240-243, Feb. 1985.

Jankov et al.; Laser intrastromal keratoplasty—case report; J. Refract.Surg.; 20(1); pp. 79-84; Jan.-Feb. 2004.

Sharma; U.S. Appl. No. 14/427,510 entitled "Corneal implant edges and methods of use,", filed Mar. 11, 2015.

Holliday et al.; U.S. Appl. No. 14/656,621 entitled "Methods of correcting vision,", filed Mar. 12, 2015.

Esguerra et al.; U.S. Appl. No. 14/688,226 entitled "Corneal implant delivery devices and methods of use,", filed Apr. 16, 2015.

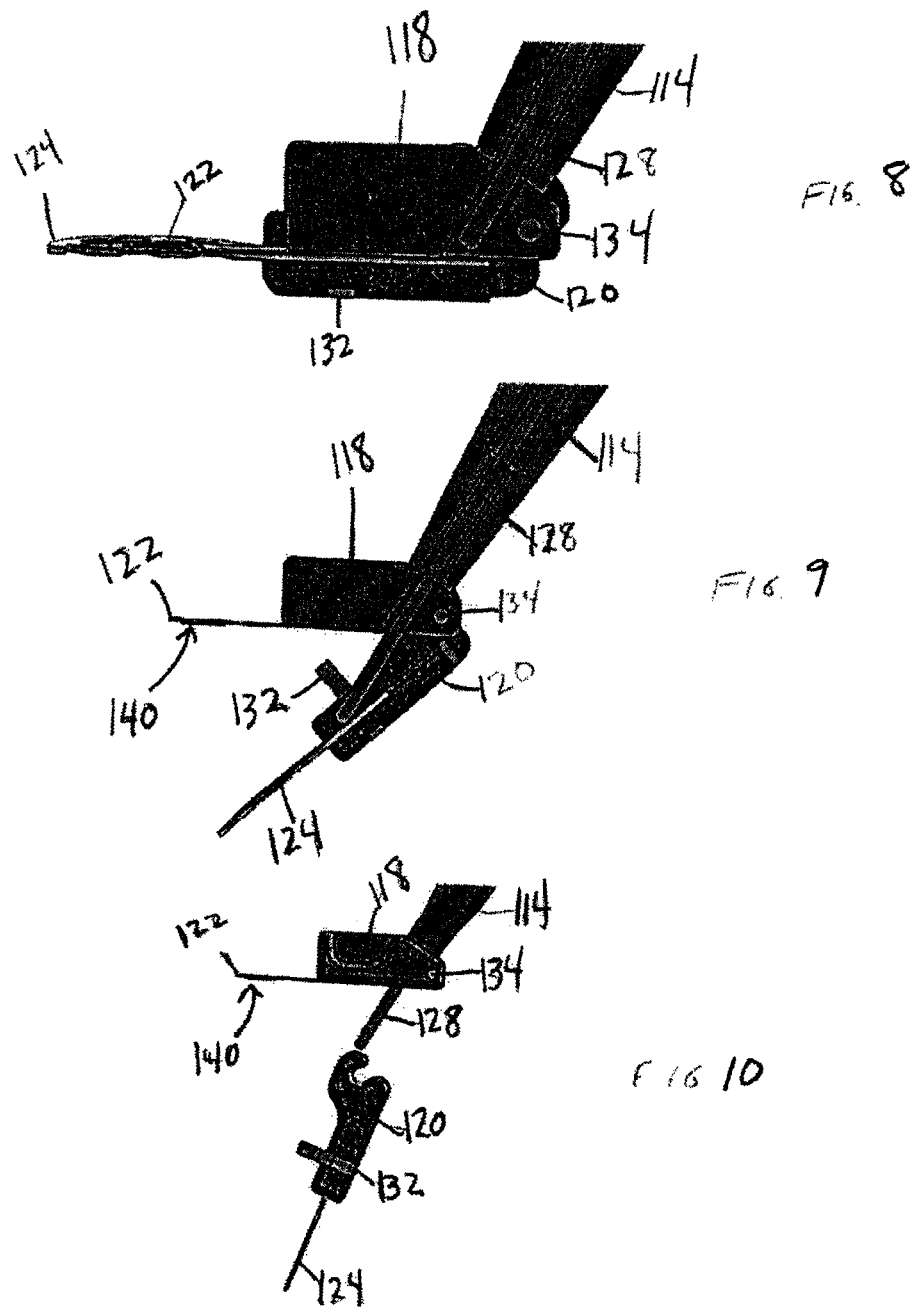

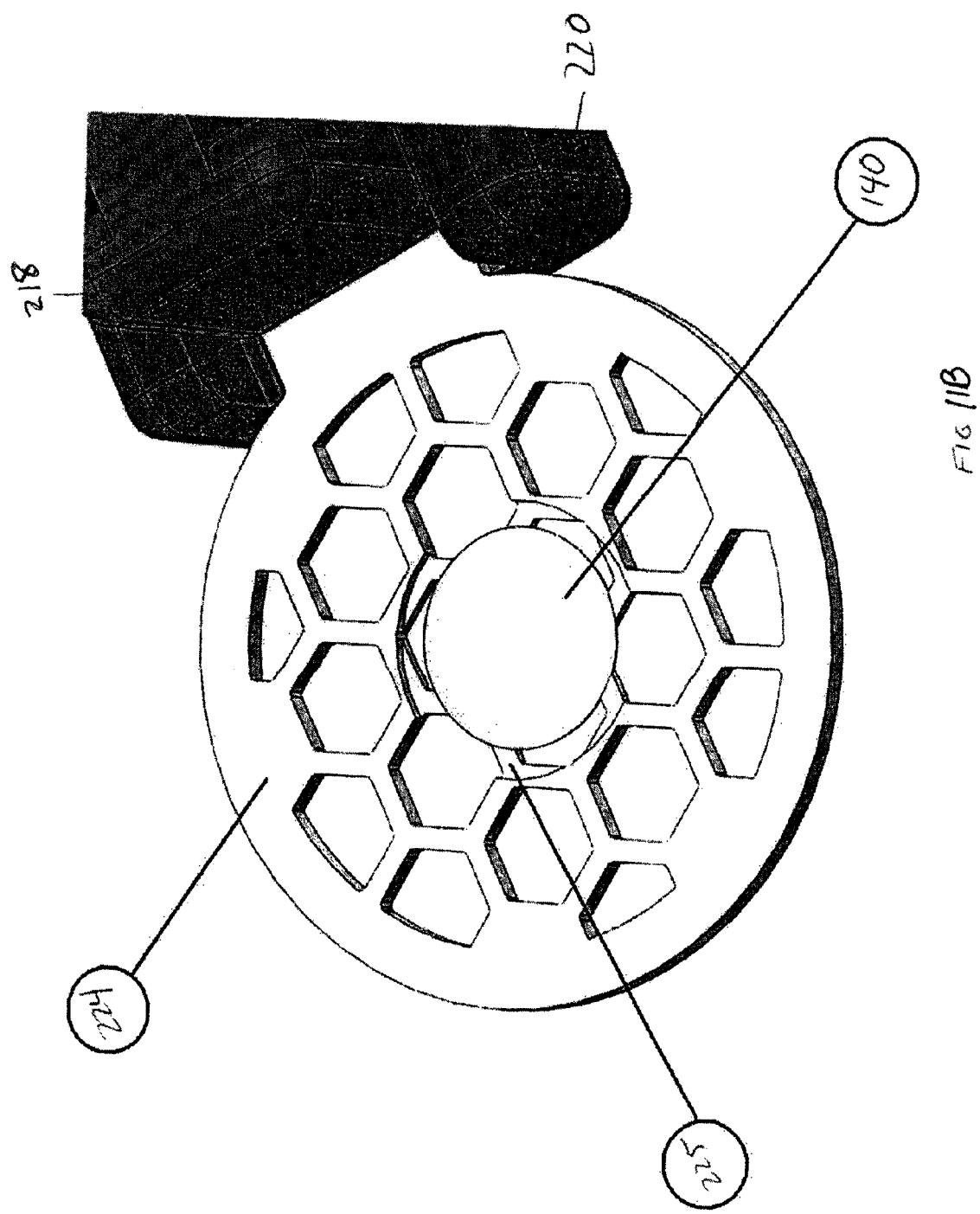

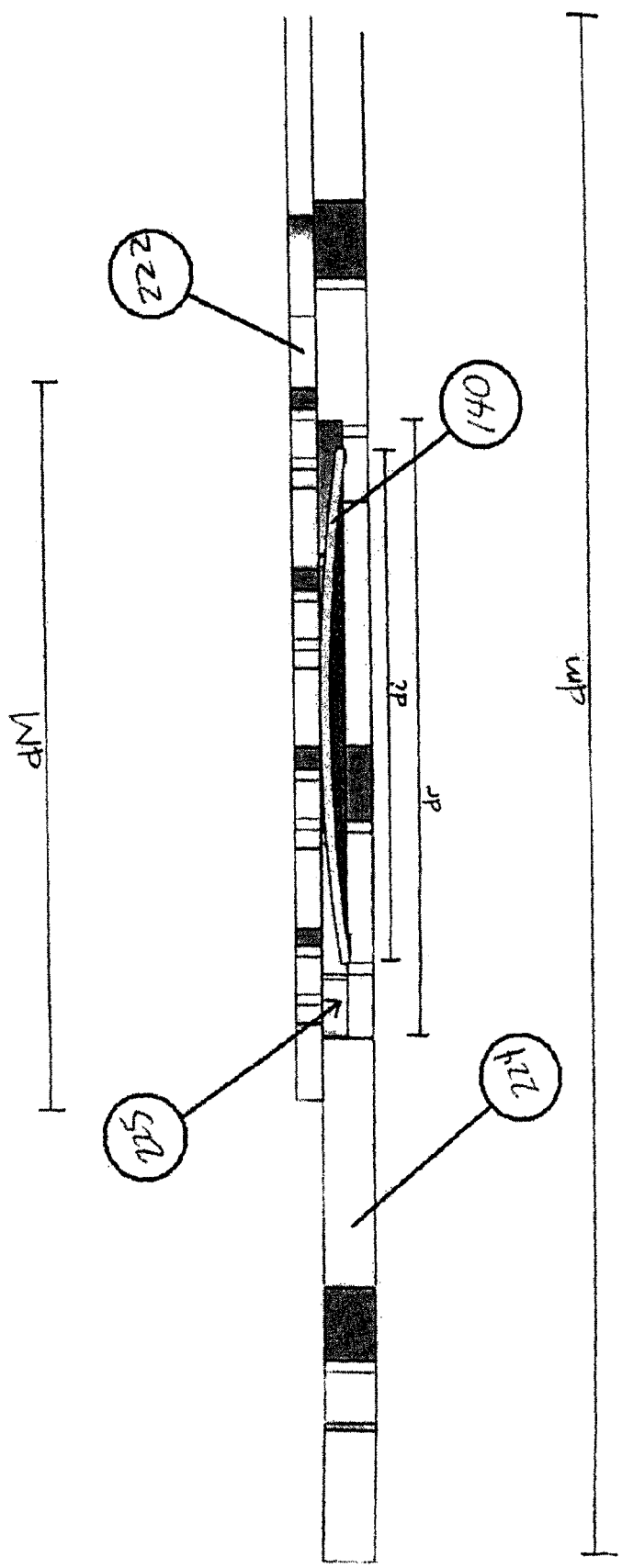

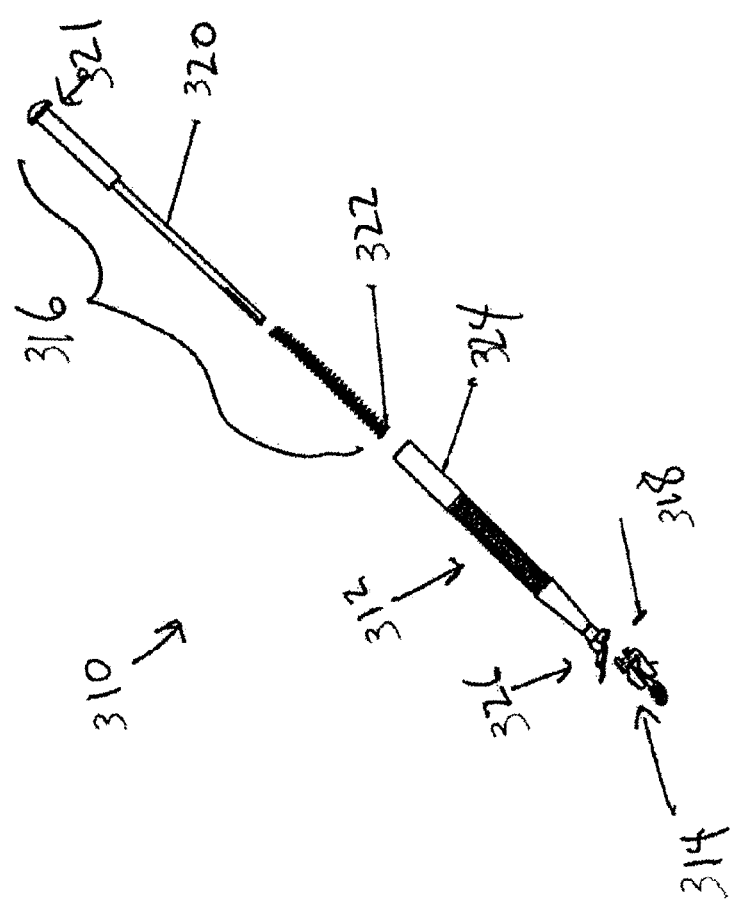

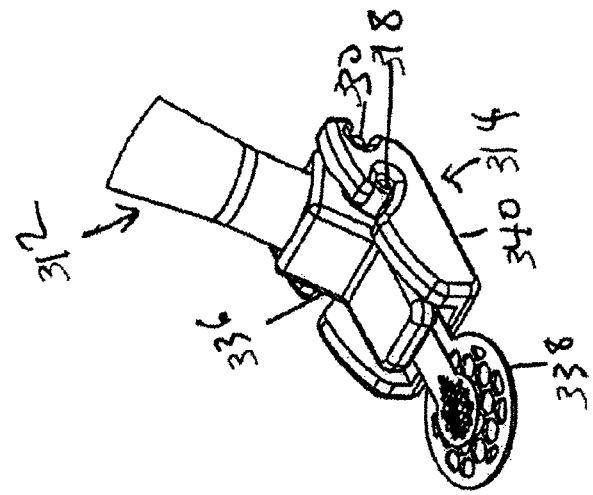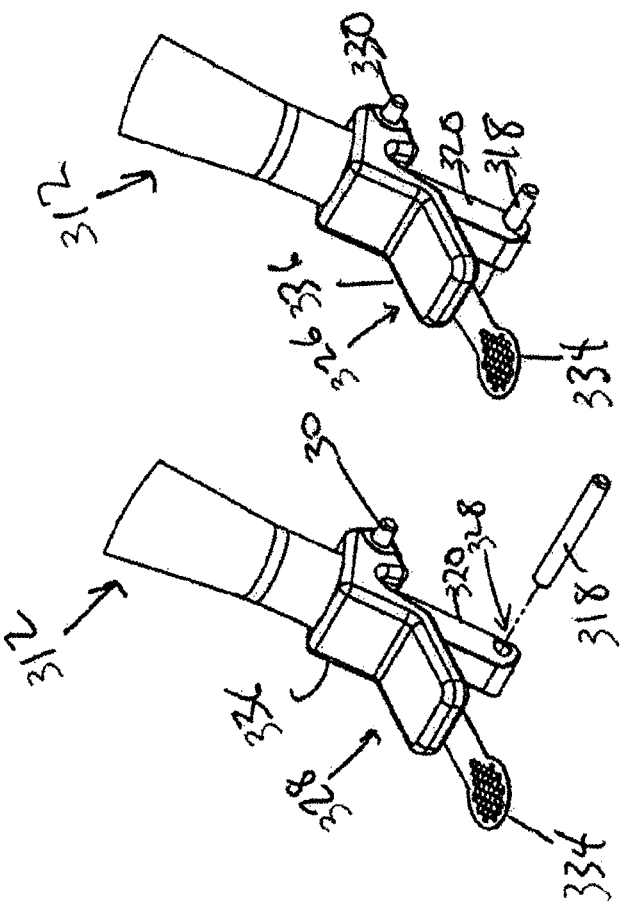

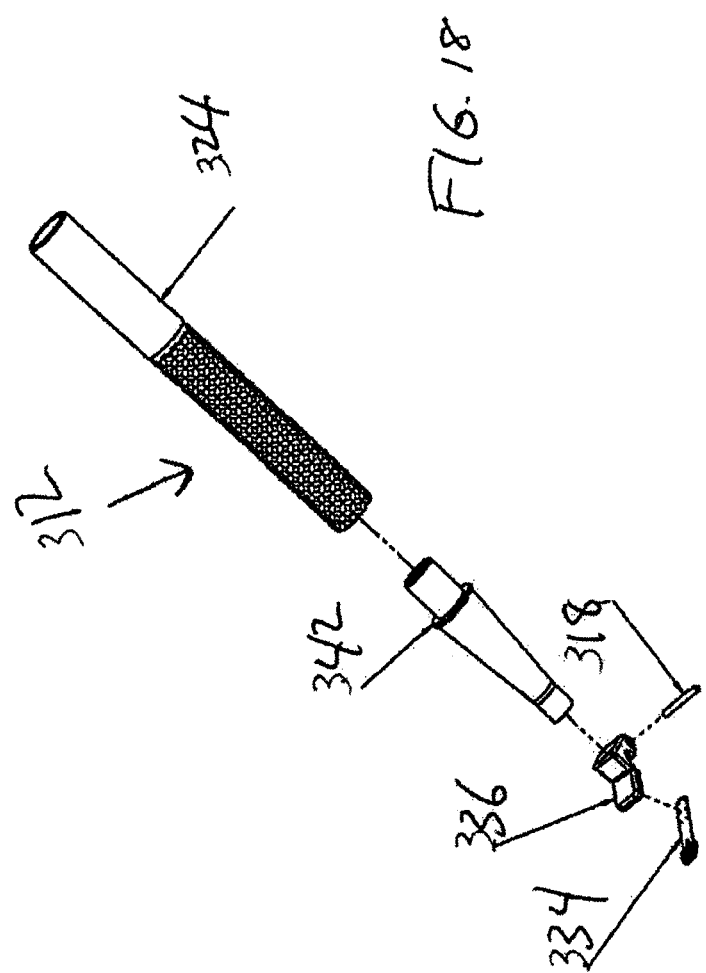

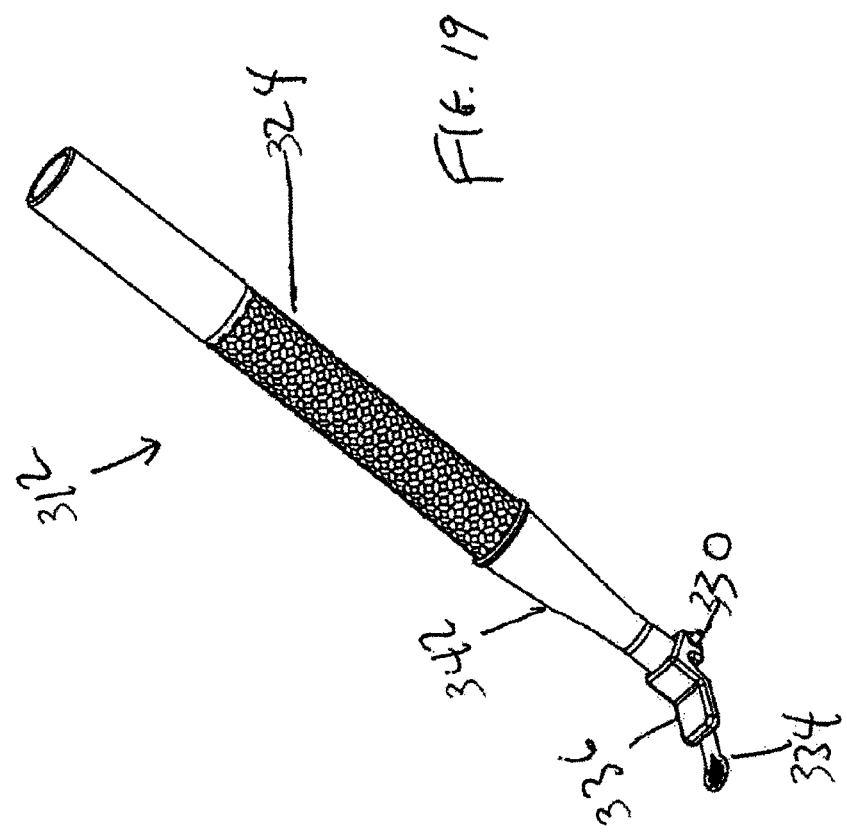

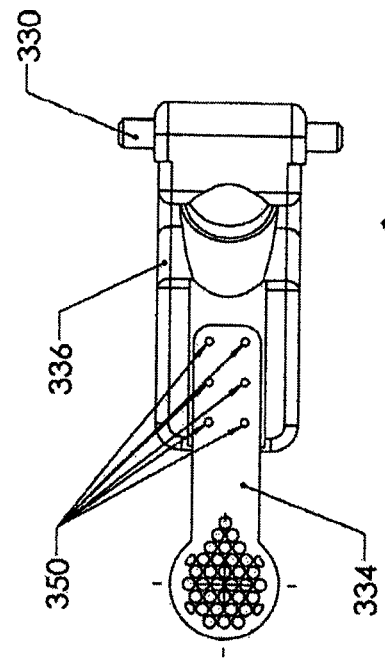
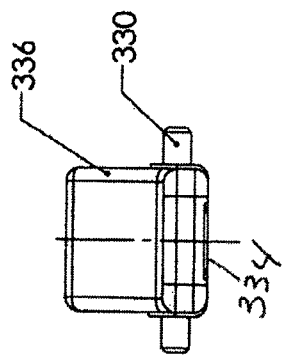
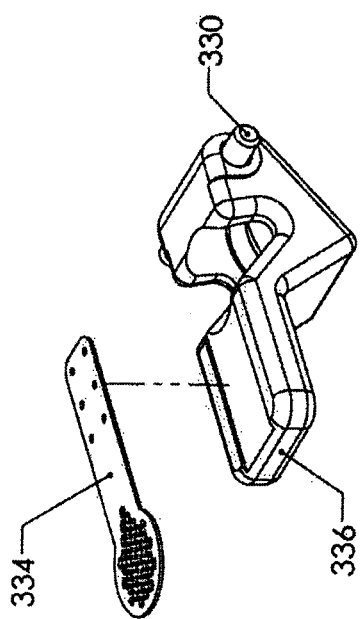
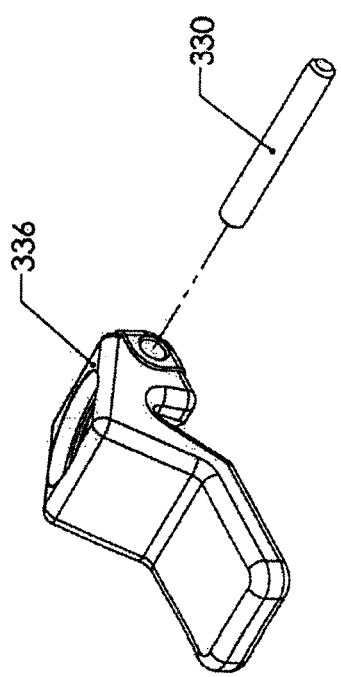
FIG. 20C
FIG. 20D
FIG. 20A
FIG. 20B

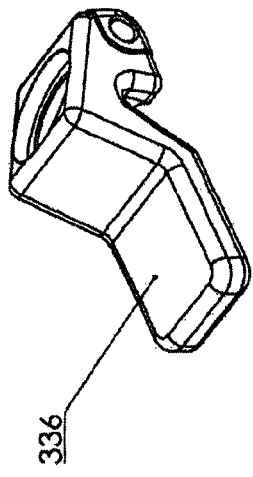
FIG. 21F
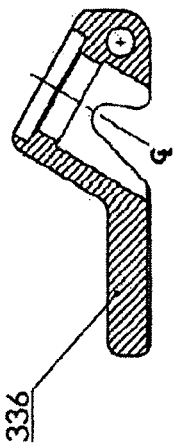
SECTION A-A
FIG. 21D
FIG. 21C
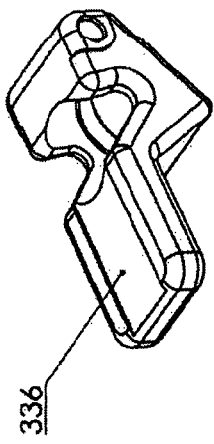
FIG. 21E
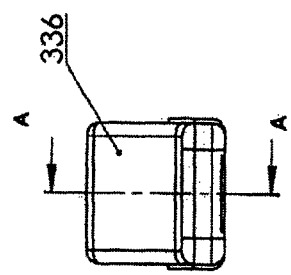
FIG. 21A
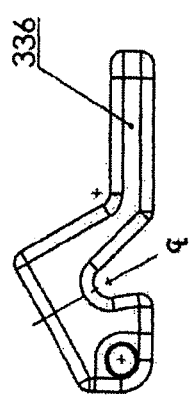
FIG. 21B
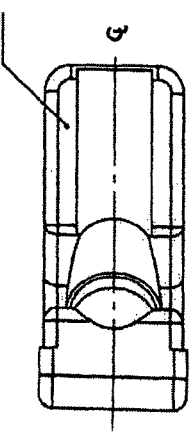

DETAIL C

SECTION B-B

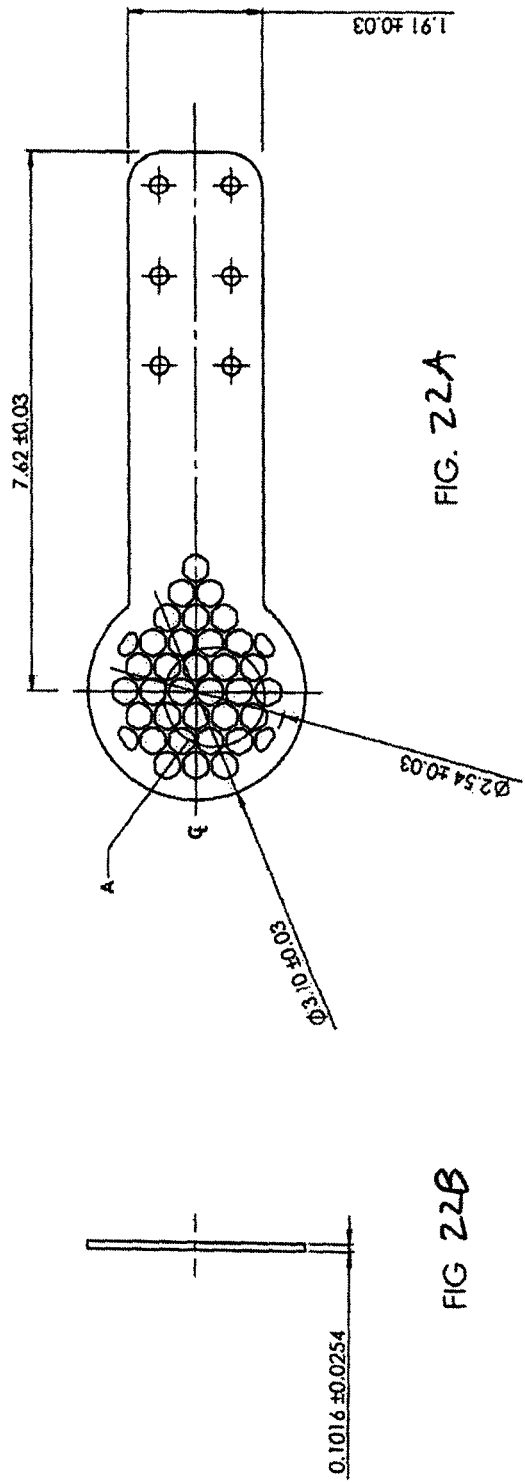
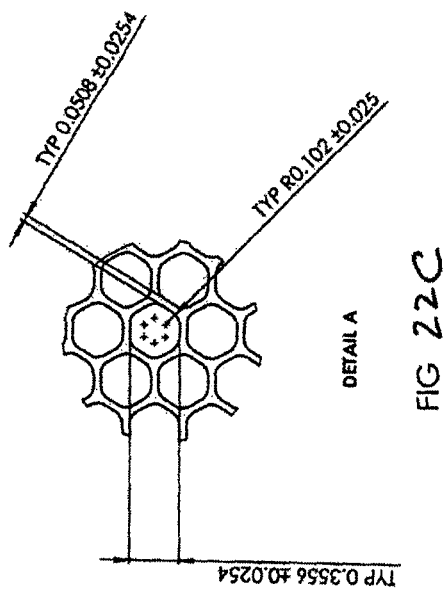
FIG. 22A
FIG. 22B
FIG. 22C

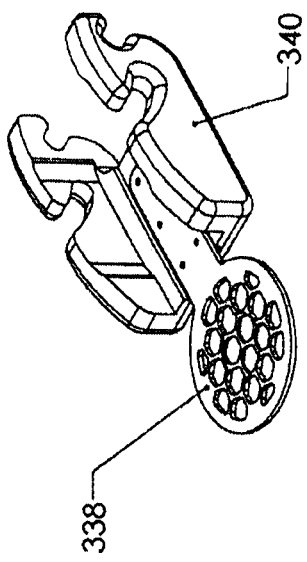
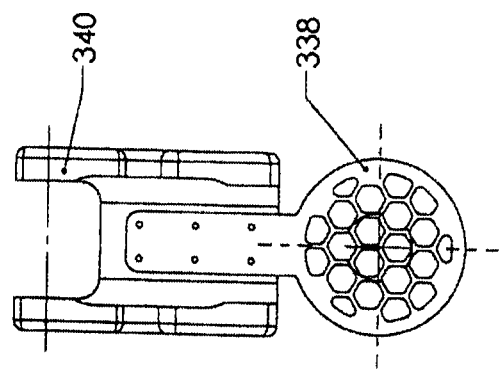
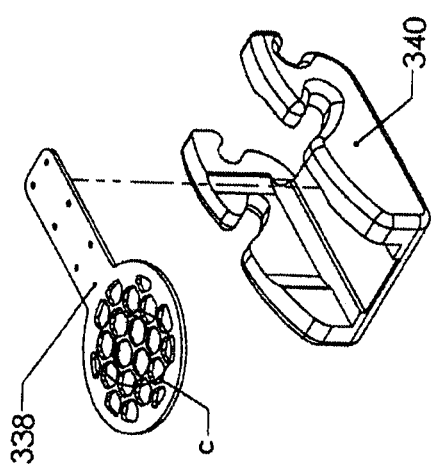
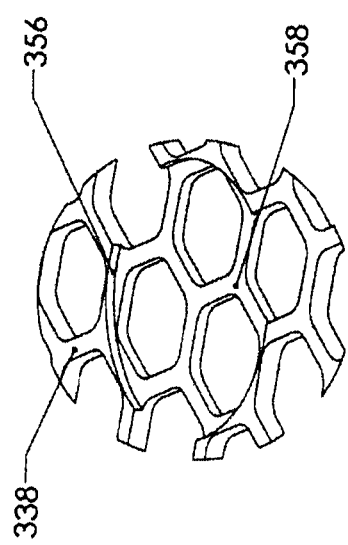

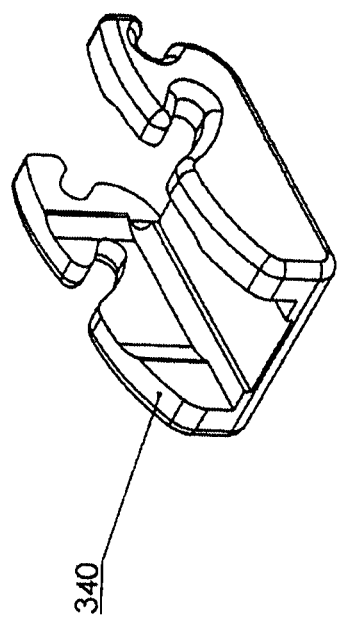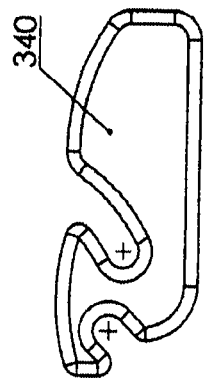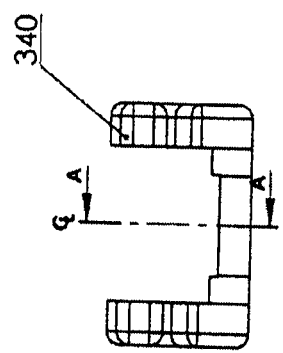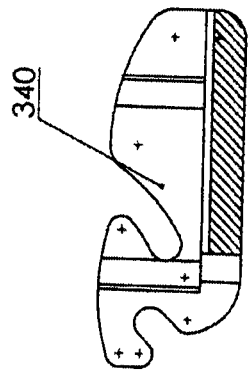
FIG. 24E
FIG. 24C
FIG. 24A
SECTION A-A
FIG. 24B

DETAIL B

SECTION A-A

DETAIL C

SECTION A-A

SECTION A-A

SCALE 1:2

SECTION A-A
SCALE 2:1

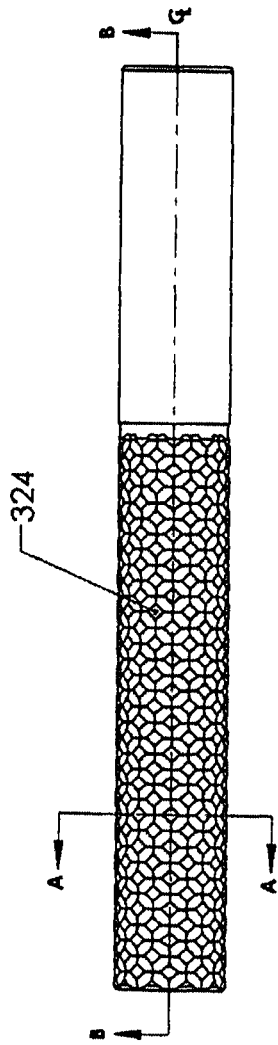
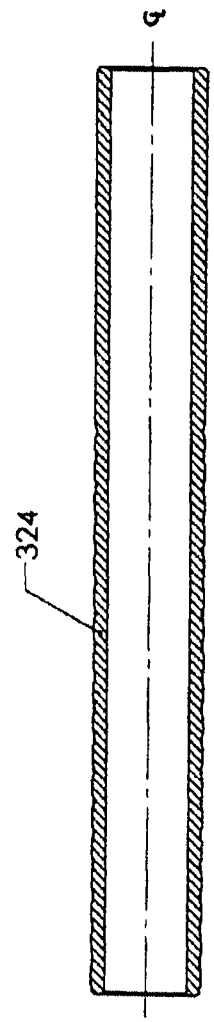
FIG. 30A
FIG. 30B SECTION B-B
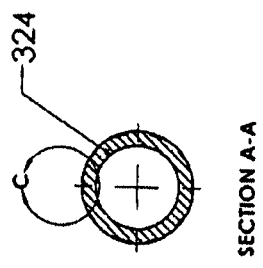
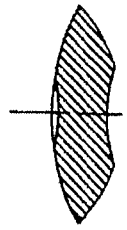
FIG. 30C SECTION A-A
FIG. 30D DETAIL C

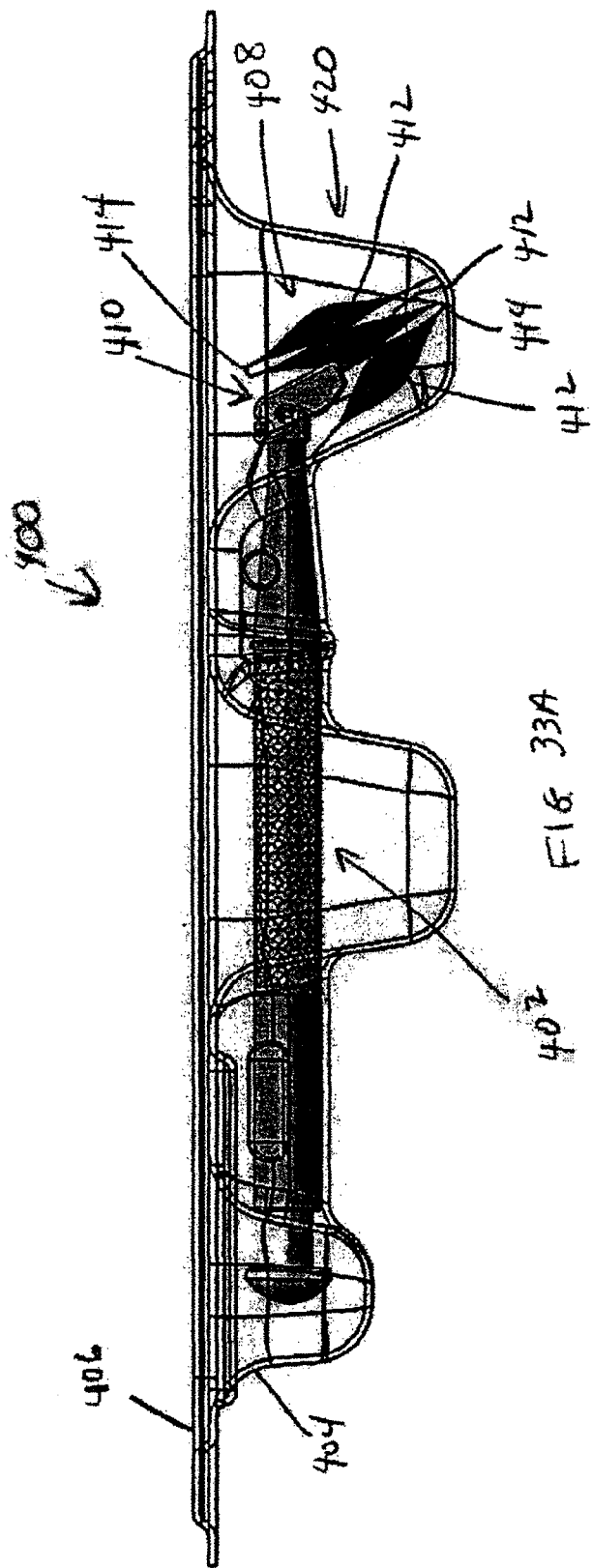

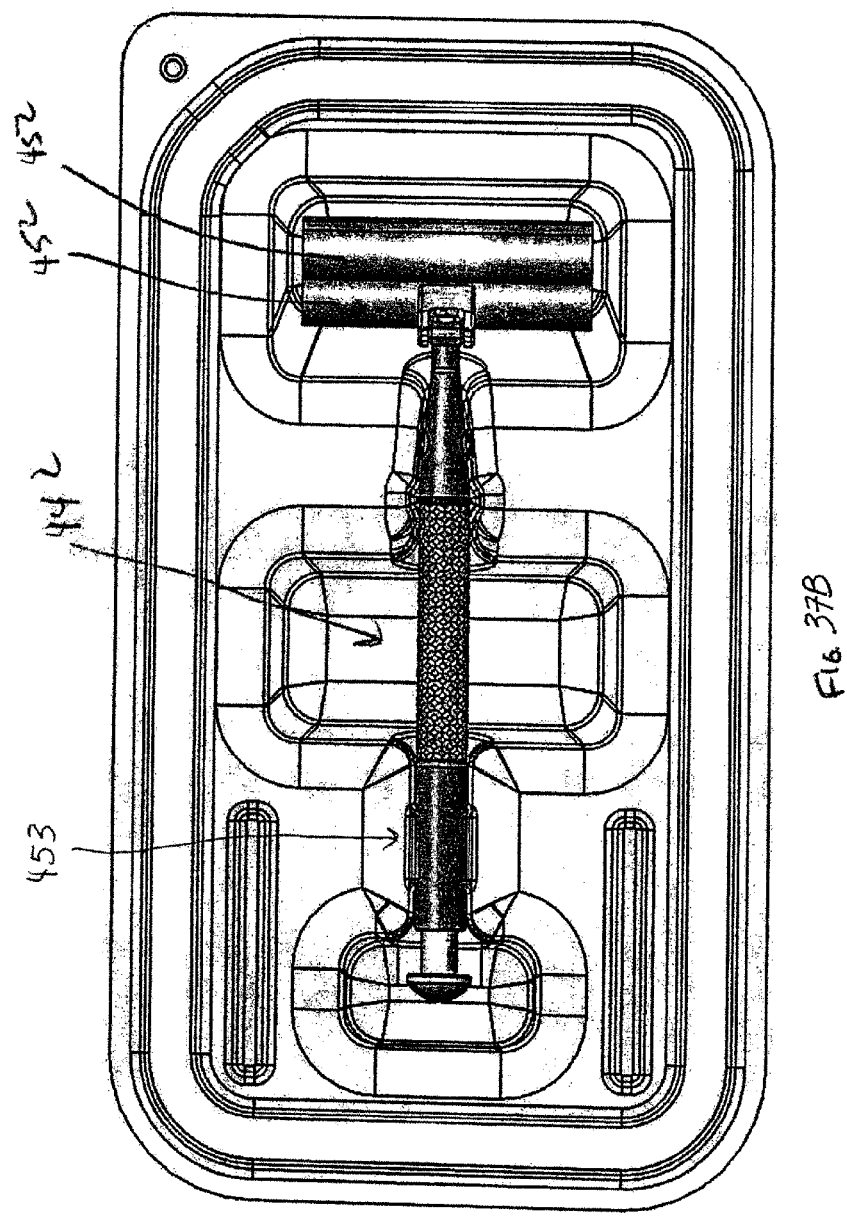

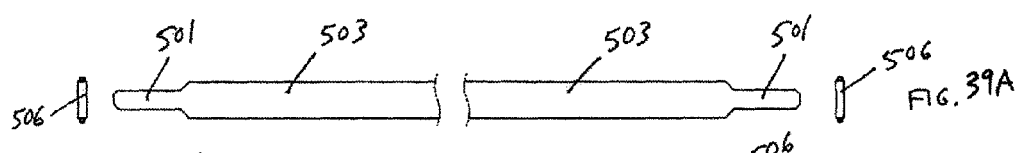
FIG. 39A
FIG. 39B
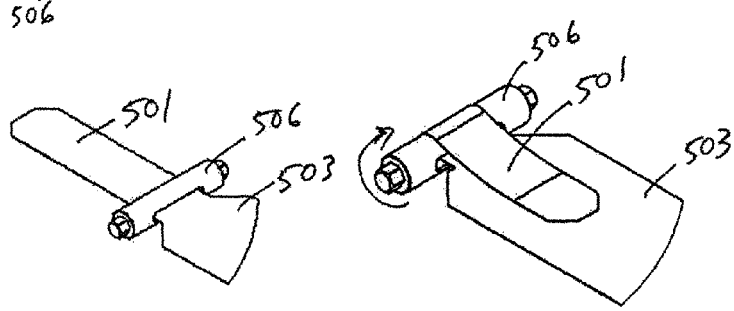
FIG. 40A
FIG. 40B

CORNEAL IMPLANT STORAGE AND DELIVERY DEVICES

CROSS REFERENCE TO RELATED APPLICATIONS

This application claims priority to the following provisional applications: U.S. 61/550,185, filed Oct. 21, 2011; U.S. 61/679,482, filed Aug. 3, 2012; and U.S. 61/606,674, filed Mar. 5, 2012; all disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Corneal implants, such as corneal onlays and corneal inlays, can be small, delicate medical devices, the storage and/or handling of which should be carefully performed to prevent damage to the implants. Additionally, corneal implants can also be transparent, which, in addition to their small size, can make them difficult to see with the unaided eye.

Devices and methods are needed that allow for easy handling and positioning of small, delicate corneal implants without damaging the implant.

Additionally, the packaging tools and assemblies described herein generally provide one or more of three functions: to surround and protect the applicator apparatus, including the corneal implant retained therein, from damage; to act as a fluid reservoir and provide fluid to the corneal implant to keep the corneal implant hydrated during storage; and to remove, or wick away, excess fluid when removing the corneal implant applicator from the packaging materials.

SUMMARY OF THE DISCLOSURE

One aspect of the disclosure is a corneal implant applicator apparatus, comprising an implant applicator with one or more applicator openings therethrough, and an implant support with one or more support openings therethrough, wherein the implant applicator and implant support are disposed relative to one another to form an implant nest, and wherein the implant nest is adapted to house a corneal implant, wherein a ratio of the sum of the perimeters of the one or more applicator openings to the sum of the areas of the one or more applicator openings is greater than a ratio of the sum of the perimeters of the one or more support openings to the sum of the areas of the one or more support openings, and wherein the greater ratio provides the applicator with a higher affinity for a corneal implant than support.

In some embodiments the implant applicator is adapted such that corneal tissue has a greater affinity for the corneal implant that the implant applicator.

In some embodiments the implant applicator has a plurality of applicator openings therethrough. The plurality of applicator openings can have the same greatest linear dimension spanning the plurality of applicator openings.

In some embodiments the implant support has a plurality of support openings therethrough. The plurality of support openings can have the same second greatest linear dimension spanning the support openings.

In some embodiments the implant applicator has a plurality of applicator openings therethrough and the implant support has a plurality of support openings therethrough. The plurality of applicator openings can have the same greatest linear dimension spanning the plurality of applicator openings and the plurality of support openings have the same second greatest linear dimension spanning the support openings. A number of the plurality of applicator openings that overlap the corneal implant when the corneal implant is disposed in the nest can be greater than a number of the plurality of support openings that overlap the corneal implant. Fluid can be retained in the corneal implant nest, and wherein the fluid is disposed within a number of the plurality of applicator openings that overlap the corneal implant due to surface tension, and wherein the fluid is disposed within a number of the plurality of support openings that overlap the corneal implant due to surface tension, wherein a volume of fluid disposed in the applicator openings that overlap the corneal implant is greater than a volume of fluid disposed in the support openings that overlap the corneal implant. At least one of the support openings that overlaps the corneal implant does not need to have fluid extending across the entirety of the opening.

In some embodiments the corneal implant applicator has a first greatest linear dimension spanning the corneal implant applicator and the implant support has a second greatest linear dimension spanning the implant support, wherein the second greatest linear dimension is greater than the first greatest linear dimension.

In some embodiments a periphery of the implant support extends further radially than a periphery of the implant applicator.

In some embodiments the implant support has a flat implant support surface that forms a portion of the nest. The implant support can comprise a recess formed therein adapted to accommodate the corneal implant.

In some embodiments the implant applicator has a flat surface that forms a portion of the nest.

In some embodiments the implant applicator has a first greatest thickness and the implant support has a second greatest thickness, wherein the second thickness is greater than the first thickness. The second thickness can be about two times the first thickness.

In some embodiments the one or more applicator openings have hexagonal configurations.

In some embodiments the one or more support openings have hexagonal configurations.

In some embodiments the corneal implant is made from a hydrophilic material.

One aspect of the disclosure is a corneal implant applicator apparatus, comprising an implant applicator with a plurality of applicator openings therethrough; and an implant support with a plurality of support openings therethrough, wherein the number of the plurality of applicator openings is greater than the number of the plurality of support openings, wherein the implant applicator and implant support are disposed relative to one another to form a corneal implant nest, and wherein the corneal implant nest is adapted to house a corneal implant such that the corneal implant is disposed adjacent the plurality of applicator openings and the plurality of support opening.

In some embodiments the greater number of applicator openings provides the applicator with a greater affinity for the corneal implant than the support.

In some embodiments the applicator is adapted such that corneal tissue has a greater affinity for the corneal implant than the applicator.

In some embodiments a number of the plurality of applicator openings that overlap the corneal implant when positioned in the nest is greater than a number of the plurality of support openings that overlap the corneal implant when the implant is positioned in the nest.

In some embodiments the plurality of applicator openings have hexagonal configurations.

In some embodiments the plurality of support openings have hexagonal configurations.

In some embodiments the corneal implant is made from a hydrophilic material.

One aspect of the disclosure is a corneal implant applicator apparatus, comprising a corneal implant applicator with a plurality of applicator openings therethrough, wherein the plurality of applicator openings have hexagonal configurations; and a corneal implant support with a plurality of support openings therethrough, wherein the plurality of support openings have hexagonal configurations, wherein the corneal implant support disposed relative to the corneal implant applicator to form a corneal implant nest therebetween.

In some embodiments the plurality of applicator openings are sized to provide the applicator with a greater affinity for the corneal implant than the support.

In some embodiments the applicator openings are sized such that corneal tissue has a greater affinity for the corneal implant than the applicator.

In some embodiments the apparatus further comprises a corneal implant disposed within the nest adjacent the plurality of applicator openings and the plurality of support openings.

In some embodiments a linear dimension between opposing sides of the plurality of hexagonal applicator openings is less than a linear dimension between opposing sides of the plurality of hexagonal support openings.

In some embodiments the corneal implant is made from a hydrophilic material.

One aspect of the disclosure is a corneal implant applicator apparatus, comprising an implant applicator with at least one applicator opening therethrough; and an implant support with at least one support opening therethrough, wherein the implant applicator and implant support are disposed relative to one another to form an implant nest that is adapted to house a corneal implant; wherein the at least applicator opening and the at least one support opening are adapted such that forces between the corneal implant and a liquid disposed in the at least one applicator opening are greater than forces between the corneal implant and a liquid disposed in the at least one support opening, wherein the greater forces provide the applicator with a greater affinity for the corneal implant than the support.

In some embodiments the at least one applicator opening are adapted to provide the applicator with less of an affinity for the corneal implant than a corneal surface.

In some embodiments the number of applicator openings is greater than the number of support openings. The number of applicator openings that overlap the corneal implant when positioned in the implant nest can be greater than the number of support openings that overlap the corneal implant.

In some embodiments the size of the at least one applicator opening is smaller than the size of the at least one support opening.

In some embodiments the implant applicator has a first surface through which the at least one applicator opening passes, wherein the first surface is flat.

In some embodiments the implant support has a first surface through which the at least one support opening passes, wherein the first surface is flat.

In some embodiments a ratio of the sum of the perimeters of the at least one applicator openings to the sum of the areas of the at least one applicator openings is greater than a ratio of the sum of the perimeters of the at least one support openings to the sum of the areas of the at least one support openings, and wherein the greater ratio provides the applicator with a higher affinity for a corneal implant than the support.

In some embodiments the at least one applicator opening and the at least one support opening have hexagonal configurations.

In some embodiments the implant applicator has a plurality of applicator openings therethrough and the implant support has a plurality of support openings therethrough, wherein the plurality of applicator openings are smaller than the plurality of support openings.

In some embodiments the implant applicator has a plurality of applicator openings therethrough and the implant support has a plurality of support openings therethrough, and wherein a number of the plurality of applicator openings that overlap the corneal implant when the corneal implant is disposed in the nest is greater than a number of the plurality of support openings that overlap the corneal implant.

In some embodiments the corneal implant is made from a hydrophilic material.

One aspect of the disclosure is a corneal implant applicator apparatus, comprising an implant applicator with a plurality of applicator openings therethrough; and an implant support with a plurality of support opening therethrough, wherein the implant applicator and implant support are disposed relative to one another to form an implant nest that is adapted to house a corneal implant, and wherein the arrangement of the plurality of applicator openings provides the applicator with a higher affinity for the corneal implant than the support.

In some embodiments the arrangement of the plurality of applicator openings provides the applicator with less of an affinity for the corneal implant than a corneal surface.

In some embodiments the number of applicator openings is greater than the number of support openings. The number of applicator openings that overlap the corneal implant when positioned in the implant nest can be greater than the number of support openings that overlap the corneal implant.

In some embodiments the size of the plurality of applicator openings is smaller than the size of the plurality of support openings.

In some embodiments the implant applicator has a first surface through which the plurality of applicator openings pass, and wherein the first surface is flat.

In some embodiments the implant support has a first surface through which the plurality of support openings pass, wherein the first surface is flat.

In some embodiments a ratio of the sum of the perimeters of the plurality of applicator openings to the sum of the areas of the plurality of applicator openings is greater than a ratio of the sum of the perimeters of the plurality of support openings to the sum of the areas of the plurality of support openings, and wherein the greater ratio provides the applicator with a higher affinity for a corneal implant than support.

In some embodiments the plurality of applicator openings and the plurality of support openings have hexagonal configurations.

In some embodiments the plurality of applicator openings are smaller than the plurality of support openings.

In some embodiments a number of the plurality of applicator openings that overlap the corneal implant when the corneal implant is disposed in the nest is greater than a number of the plurality of support openings that overlap the corneal implant.

In some embodiments the corneal implant is made from a hydrophilic material.

One aspect of the disclosure is a corneal implant hydration control apparatus, comprising a body forming a pocket configured to receive and stabilize a corneal implant delivery apparatus therein.

In some embodiments the body comprises a first hydration control element and a second hydration control element disposed relative to the first hydration control element to form the pocket. The first and second hydration control elements can comprise sections of rolled up material. The first and second hydration control elements can comprise sections of rolled up material from an integral section of material. A section of the integral section of material can form a backstop. The first and second hydration control elements can be generally cylindrically-shaped. The first and second hydration control elements can engage one another.

In some embodiments the apparatus further comprises a first deformable base secured to the body, wherein the first deformable base is adapted to deform to adjust a distance between a first hydration control element and a second hydration control element, wherein the first and second hydration control elements form at least a portion of the pocket. The apparatus can further comprise a first core disposed within the first hydration control element and a second core disposed within the second hydration element, wherein the first deformable base is secured to the first and second cores to secure the base to the first and second hydration control elements. The apparatus can further comprise a second deformable base second to the first and second cores. The first deformable base can be secured to a first end of each of the first and second cores, and the second deformable base is secured to a second end of each of the first and second cores. The first deformable base can include a living hinge that allows the deformable base to deform to adjust the distance between the first and second hydration control elements.

In some embodiments the pocket has a general wedge shape formed by a first and second hydration control elements.

In some embodiments the body is formed of a polyester material.

In some embodiments the body is adapted to wick away fluid from an apparatus disposed within the pocket as the apparatus is removed from the pocket.

One aspect of the disclosure is a packaging assembly for a corneal implant applicator, comprising a corneal implant applicator apparatus comprising an implant portion in which a corneal implant is retained; a hydration control member comprising a pocket that is adapted to receive and stabilize the implant portion therein.

In some embodiments the implant portion in which the corneal implant is retained is substantially flat.

In some embodiments the corneal implant is retained in the implant portion of the corneal implant applicator apparatus in a substantially unstressed configuration.

In some embodiments the hydration control member comprises a first hydration control element and a second hydration control element, wherein the first and second hydration control elements form at least a portion of the pocket. The first and second hydration control elements are generally cylindrically shaped.

In some embodiments the hydration control member further comprises a backstop adapted to prevent the corneal implant applicator apparatus from being advanced too far within the pocket.

In some embodiments the first and second hydration control elements are adapted to be moved apart from one another to accommodate the corneal implant applicator apparatus.

One aspect of the disclosure is a method of removing excess storage liquid from a corneal implant applicator apparatus, comprising providing a corneal implant applicator apparatus, wherein a corneal implant is disposed within a portion of the apparatus; and stripping excess fluid from the portion of the apparatus by engaging the portion of the apparatus in which the implant is disposed with a hydration control member while moving the portion of the apparatus with respect to the hydration control member.

In some embodiments the portion of the apparatus includes first and second surfaces each with at least one opening formed therein, the first and second surfaces forming a corneal nest, wherein the stripping step comprises removing excess fluid away from the first and second surfaces.

In some embodiments the stripping step comprises engaging the portion of the apparatus with first and second hydration control elements while moving the portion of the apparatus with respect to the first and second hydration control elements.

One aspect of the disclosure is a method of storing a corneal implant applicator apparatus, comprising providing a corneal implant applicator apparatus with a first portion in which a corneal implant is positioned; positioning the first portion of the apparatus into a pocket formed by a hydration control member until the first portion engages the hydration control member.

In some embodiments the positioning step creates a fluid communication between the hydration control member and the corneal implant.

In some embodiments the positioning step comprises advancing the first portion into a pocket formed by two hydration control elements until the first portion engages the two hydration control elements. The positioning step can comprise positioning a first apparatus surface into engagement with a first hydration control element and positioning a second apparatus surface into engagement with a second hydration control element.

BRIEF DESCRIPTION OF THE DRAWINGS

FIGS. 4-10 illustrate an exemplary corneal implant applicator apparatus.
FIGS. 16-19 illustrate an exemplary corneal implant applicator apparatus.
FIGS. 20A-32B illustrate components of an exemplary corneal implant applicator apparatus.
FIGS. 33A-33B illustrate a portion of an exemplary corneal implant applicator apparatus positioned within a pocket of a hydration control member and within a packaging tray.
FIGS. 37A-37B illustrate a portion of an exemplary corneal implant applicator apparatus positioned within a pocket of a hydration control member and within a packaging tray.

FIGS. 38A-40B illustrate an exemplary hydration control member.

DETAILED DESCRIPTION

The disclosure relates to devices for one or more of packaging, storing, positioning, and delivering corneal implants such as corneal inlays. The devices herein can be used in the movement and positioning of, for example without limitation, corneal onlays, corneal inlays, corneal replacements, and contact lenses.

The disclosure includes devices and methods of use that rely at least partially on surface tension of liquids to control the positioning and/or movement of a corneal implant. The devices can be used in the storage, packaging, movement, or delivering of the corneal implants. These approaches can be used when the corneal implant is made at least partially of hydrophilic material, such as a hydrogel.

Figure 1:
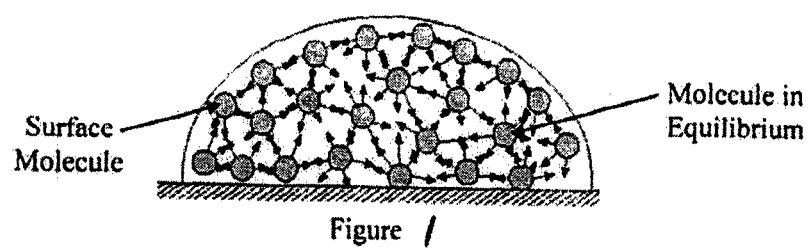
FIG. 1 illustrates exemplary cohesive forces.

Surface tension is the property of liquids that allows the surface of a body of liquid to resist external forces. It is what allows objects denser then water, such as small pins and certain insects, to float on a liquid's surface. Surface tension is caused by the cohesive forces of a liquid's molecules. Cohesive forces are the attractive forces between two like molecules. As shown in FIG. 1, an average molecule within a body of liquid has no overall cohesive force acting upon it because it sees cohesive forces from neighboring molecules acting upon it in every direction. A molecule on the surface, however, only sees cohesive forces pulling it inwards. For very small droplets, the inward force on all surface molecules causes the droplet to be generally spherical in shape.

Figure 2:
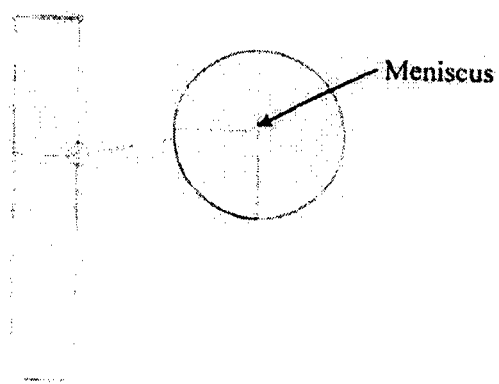
FIG. 2 illustrates exemplary adhesive forces.

Adhesive forces, on the other hand, are those seen between unlike molecules. For some material combinations, these forces can be greater than the cohesive forces of a liquid's molecules. These strong adhesive forces are the cause of an upward 'bowing,' called the meniscus (as shown in FIG. 2), in a liquid's surface where the liquid around the edge of a container is pulled higher than the rest of the surface by the adhesive forces between the liquid and the container. The adhesive forces pull up on the surface of the water and are in equilibrium with the gravitational forces pulling down on the body of liquid.

Figure 3:
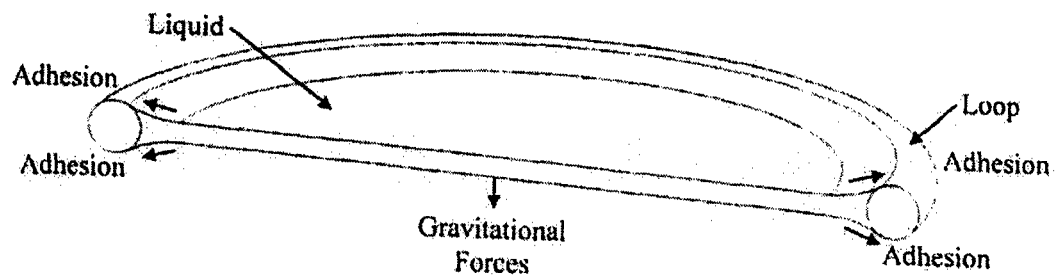
FIG. 3 illustrates a liquid suspended within a loop

In the case of liquid suspended within a loop, as shown in FIG. 3, adhesion forces from the loop act on both the top and bottom surfaces of the liquid and cohesive forces act across both upper and lower surfaces. These forces are sufficient to hold a liquid within a loop up until the liquid's volume is so great that the gravitational forces overcome the cohesive and adhesive forces.

In the case of a solid, mesh, or other such surface, the adhesive and cohesive forces act in a similar fashion. Many factors, including the type of material, the type of fluid, and the surface geometry will affect the strength of the adhesive and cohesive forces.

Exemplary corneal implants that can be stored and used in the following embodiments are corneal inlays described in U.S. Pub. No. US 2007/0203577, filed Oct. 30, 2006, U.S. Pub. No. US 2008/0262610, filed Apr. 20, 2007, and U.S. Pub. No. 2011/0218623, filed Sep. 8, 2010, the disclosures of which are incorporated herein by reference. In some embodiments, a "small diameter" (i.e., between about 1 mm and about 3 mm) corneal inlay is made from a hydrogel, that may be primarily fluid. This, as well as the inlay's small size, causes it to behave in somewhat the same way as a fluid. The disclosure below makes use of these characteristics of the corneal implant and the adhesion forces between a fluid and various surface geometries. While the disclosure herein focuses on corneal inlays, any corneal implant that exhibits similar properties can be used as described herein. For example, corneal onlays, at least a portion of which have hydrophilic properties, can be used as described herein.

The devices herein rely on a body's "affinity" for a fluid or an object with fluid-like properties (e.g., a hydrophilic corneal implant). As used herein, a body's "affinity" for the fluid or fluid-like object is influenced by the difference between the strength of the net adhesive forces between the body and the fluid or fluid-like object and the strength of the net cohesive forces within the fluid or fluid-like object. In embodiments herein where there is a substantially constant fluid or fluid-like object (e.g., a hydrophilic corneal inlay), the relative affinities of two bodies for the fluid or fluid-like object is at least partially determined by the relative strengths of the net adhesive forces between the bodies and the fluid or fluid-like object. For example, in an embodiment in which the fluid-like object is a hydrophilic corneal implant, a first body can have a greater affinity for the implant than a second body when the net adhesive forces between the first body and the implant are greater than the net adhesive forces between the second body and the implant.

The corneal implant will remain adhered to the body with the highest net force (the sum of the adhesive and cohesive forces).

A first body, referred to herein as a "moderate body," has a greater affinity for the fluid or fluid-like object than a second body, referred to herein as a "minimal body." As used herein in this context, "body" may be used interchangeably with device, component, structure, or other similar term to indicate anything with structure. The eye, however, has a greater affinity for the fluid or fluid-like object than the moderate body. The different relative affinities can be used to handle the inlay and control the movement of the inlay as it is moved from one surface to another without a user needing to touch it with a hand or other tool. Factors that influence the relative affinities include one or more of: the type of material, the type of fluid, and the surface geometry including surface area.

As used herein, a corneal inlay (e.g., the fluid-like object) has a greater "affinity" for the corneal bed of the eye than it does the moderate body, and at the same time the inlay has a greater affinity for the moderate body than it does the minimal body. The eye can be described as having a greater affinity for the inlay than both the moderate body and the minimal body. Similarly, the moderate body can be described as having a greater affinity for the inlay than the minimal body. That is, the affinity between two bodies can be described relative to either body. That is, for example, the moderate body has a greater affinity for the inlay than does the minimal body, and thus the inlay will preferentially adhere to the moderate body over the minimal body.

In some embodiments the storage fluid is water or saline, for example. Water molecules are highly polarized, which provides for attractive forces with other materials.

A relative comparison of the affinity between each body and the inlay can be represented by: corneal tissue>moderate body>minimal body. The moderate and minimal bodies may take on many forms, including, without limitation, meshes, membranes, and/or material with different surface finishes or contours.

Due to the differences in affinity between the minimal body and the moderate body, the inlay preferentially remains adhered to the moderate body. It continues to adhere to the moderate body until exposed to a stronger adhesive force. The minimal and moderate bodies can therefore be any suitable material as long as the adhesive forces between the moderate body and the inlay are greater than the adhesive forces between the minimal body and the inlay. The moderate body has a greater affinity for the inlay than does the minimal body, and the adhesive properties of the materials is a factor influencing those affinities.

Figure 4:
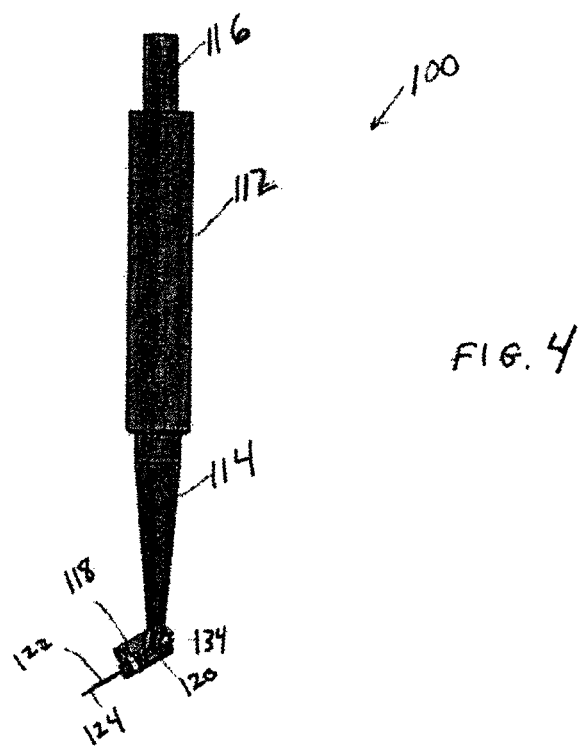
Figure 5:
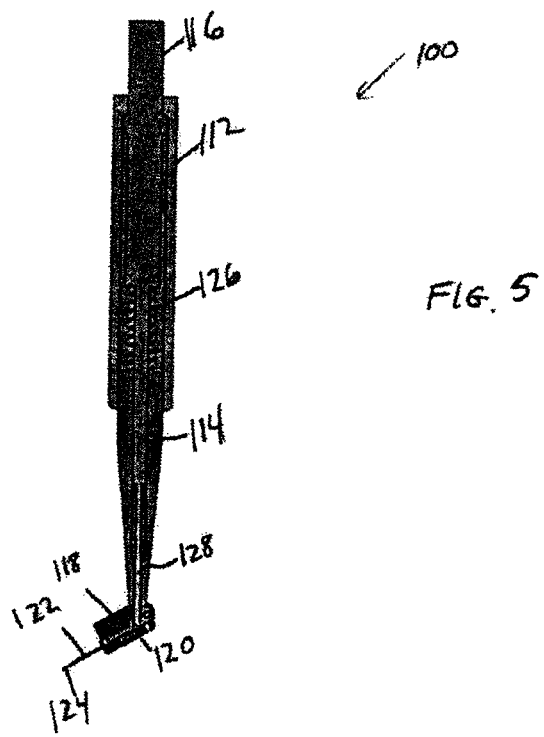

FIGS. 4-11D illustrate an exemplary embodiment of an apparatus that comprises a moderate body and a minimal body, wherein the apparatus also includes an actuation mechanism that is used to separate the minimal body from the corneal implant and the moderate body. The apparatus can be used to store the corneal implant, prepare the corneal implant for delivery, and/or deliver the corneal implant onto or into the eye. FIGS. 4 and 5 (side view and sectional side view, respectively) illustrate device 100 including handle 112 secured to distal portion 114. Actuator 116 is disposed in both handle 112 and distal portion 114, both of which are adapted to allow actuator 116 to pass therethrough. Spring 126 maintains actuator 116 in the at-rest, or non-actuated, configuration shown in FIGS. 4 and 5. Actuator 116 has a distal section 128 with a reduced size that is disposed in a smaller sized distal channel in distal portion 114.

Figure 6:
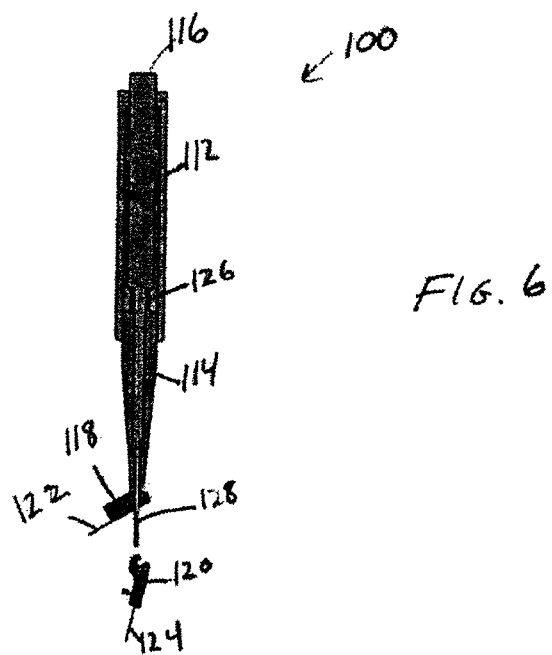

The distal end of apparatus 100 includes first portion 118 secured to moderate body 122. A second portion 120 is secured to minimal body 124 and is also detachably secured to first portion 118 around pin 134. The corneal implant (not shown in FIGS. 4 and 5 for clarity) is disposed between the moderate body and the minimal body in a nest formed by the moderate and minimal bodies. Second portion 120 is adapted to rotate with respect to first portion 118 around pin 134. FIG. 6 (sectional side view) illustrates the device after actuator 116 has been pressed down. When actuator 116 is pressed, spring 126 is compressed, and distal section 128 moves forward, or distally, through the channel in distal portion 114. The distal end of distal section 128 makes contact with second portion 120, forcing it downward as it rotates around pin 134. Because the corneal implant has a higher affinity for moderate body 122 than minimal body 124, the corneal implant will remain adhered to moderate body 122 as second portion 120 and minimal body 124 are rotated away from first portion 118 and moderate body 122. Once the curved portion of second portion 120 clears pin 134, second portion 120 is detached from first portion 118 and therefore from device 100, preparing the corneal implant for delivery (or, in some embodiments the corneal implant is delivered using a separate delivery device).

Figure 7:
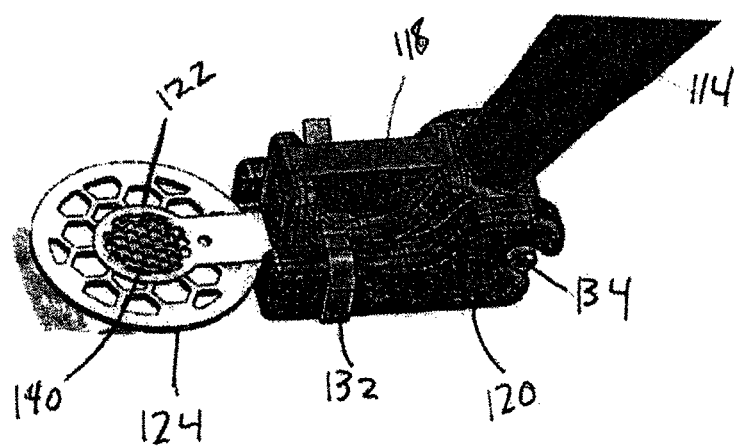

FIG. 7 illustrates a perspective view of the distal region of device 100. First portion 118 is secured to second portion 120 with clip 132, which is biased to the closed configuration shown in FIG. 7. Upon the application of the actuation force from actuator 116, clip 132 is forced into an open configuration, allowing second portion 120 and minimal body 124 to be rotated away from first portion 118.

FIG. 8 illustrates a sectional side view of the distal portion of the device. FIG. 9 shows the sectional side view from FIG. 8 after actuator 116 has been actuated and second portion 120 is rotating away from first portion 118. Corneal implant 140 remains adhered to moderate body 122 due to the higher affinity of the moderate body. FIG. 10 illustrates a side view after second portion 120 has been completely disengaged from first portion 118. Actuator 116 is then released to cause distal section 128 to retract back into distal portion 114. Corneal implant 140 is now ready for delivery and can be delivered as described above. In some embodiments the corneal implant is positioned against stromal corneal tissue, and because the inlay has a higher affinity to the corneal tissue than to the moderate body, the inlay will disassociate from the moderate body and adhere to the corneal tissue.

FIGS. 11A-11D illustrate an exemplary embodiment of minimal and moderate bodies, which can be incorporated into the assembly from FIGS. 4-10. Minimal body 224 includes recess 225 formed therein such that when moderate body and minimal body are moved towards one another, they form a nest in which the inlay is retained (see FIG. 11D). The recess has a generally circular configuration (similar to the general configuration of minimal body 224), but other configurations may be suitable. Recess 225 is adapted to accommodate the corneal implant within the recess. Recess 225 is also sized to prevent inlay 140 (see FIGS. 11B-11D) from being compressed between the minimal and moderate bodies while being shipped or stored (see FIG. 11D). The corneal implant is therefore maintained in substantially unstressed, or non-deformed, configuration. Because the inlay has a defined curvature, it may be preferred to not allow the inlay to be distorted during shipping and/or storage, and the recess (and thus the nest) can be sized to help prevent it from being distorted. Additionally, because of the fluidic nature of some inlays, it can be difficult to constrain the inlay laterally between two parallel surfaces without the presence of a recess. The recess formed in the minimal body allows for easy containment without excess force being applied to the inlay. The nest formed by the moderate and minimal bodies prevents compression and/or damage to the inlay while acting as a storage compartment.

Figure 11A:
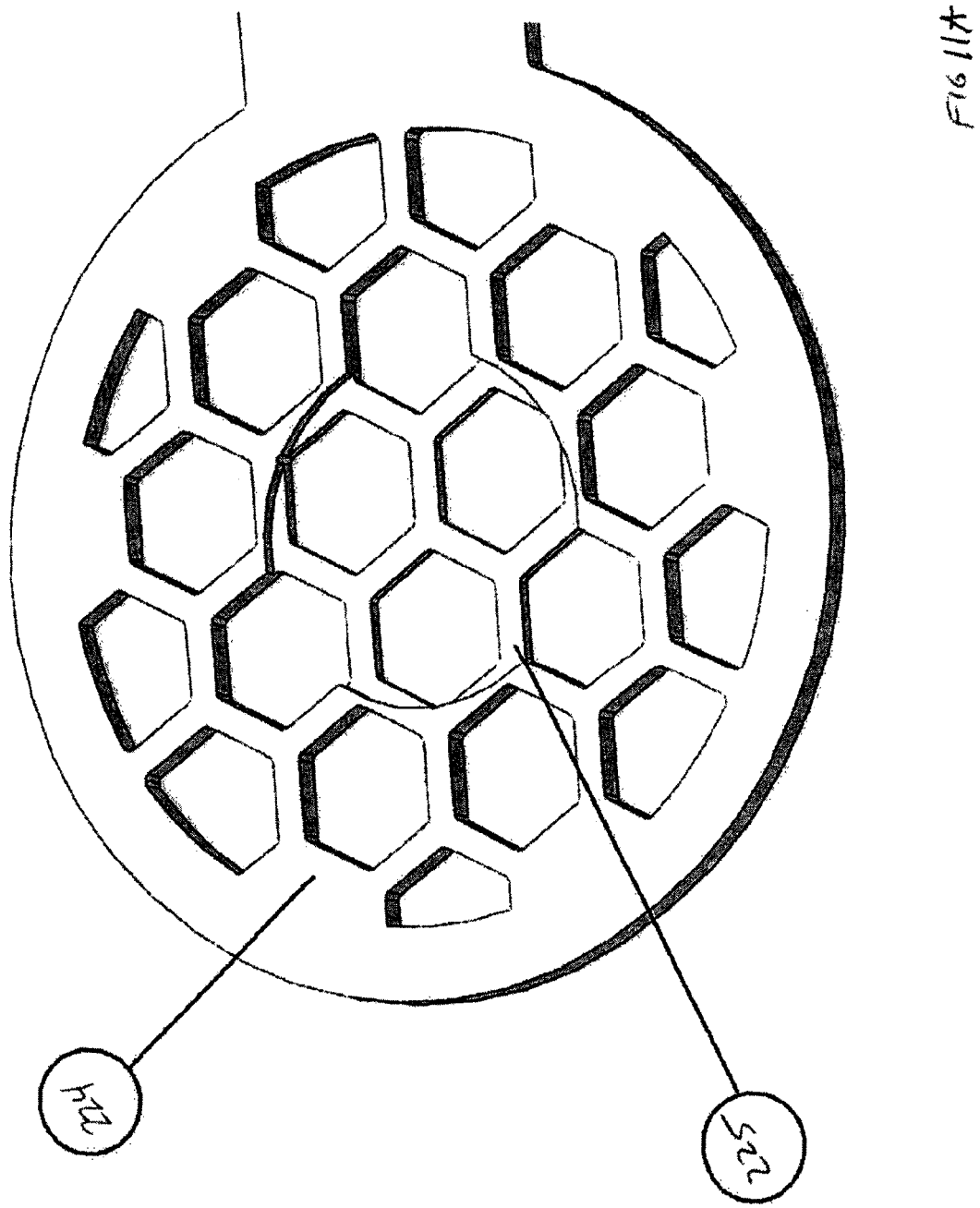
FIGS. 11A-15 illustrate exemplary moderate and minimal bodies.
Figure 11C:
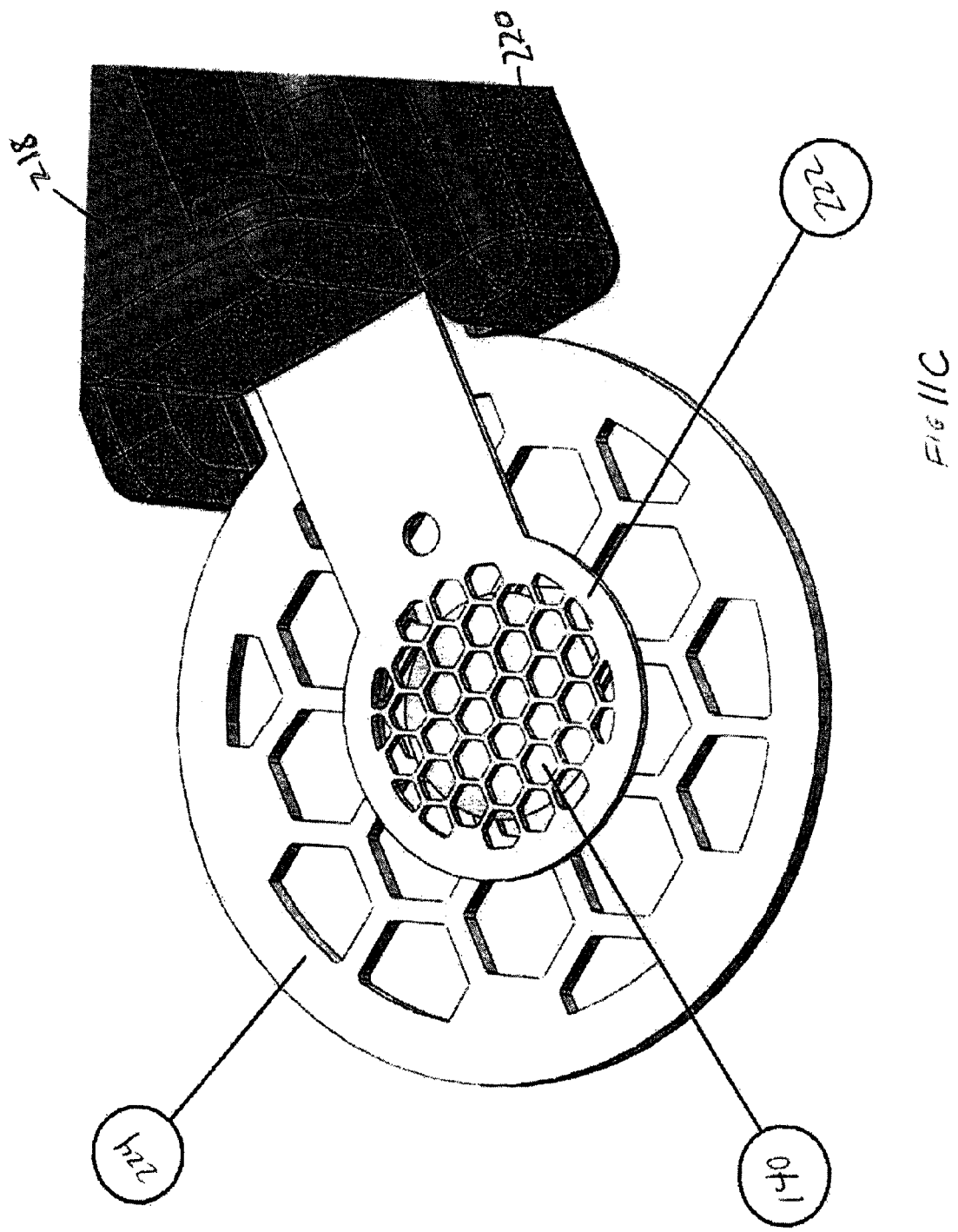

As can be seen in FIGS. 11B-11D, the recess size is larger than the inlay size. Particularly, in this embodiment, the diameter of the recess ("dr") is greater than the diameter of the inlay ("di"). Additionally, the diameter of the moderate body ("dM") is greater than the diameter of the recess ("dr") formed in the minimal body (see FIG. 11D). The diameter of the minimal body ("dm") is greater than the diameter of the moderate body ("dM").

The depth of the recess is greater than the material thickness of the inlay, but is preferably slightly less than the height of the corneal implant in a non-stressed configuration. This ensures that at least a portion of the corneal implant is maintained in contact with both the moderate body and the minimal body. If at least a portion of the corneal implant is not in contact with the moderate body, the corneal implant can remain adhered to the minimal body rather than the moderate body when the moderate and minimal bodies are moved away from one another. In an exemplary embodiment the material thickness of the corneal implant is about 38.1 microns, the overall height of the implant in a non-stressed configuration is about 152.4 microns, and the depth of the recess is between about 63.5 microns and about 114.3 microns.

Similar to the embodiment in FIGS. 4-10, moderate body 222 is secured to first portion 218, while minimal body 224 is secured to second portion 220. The system is used in the same manner as the embodiment in FIGS. 4-10.

In some exemplary embodiments of the systems shown herein (e.g., those in FIGS. 4-11D), the moderate body is stainless steel. In some embodiments it can be about 0.1 mm thick. As shown in the figures, the plurality of openings in the moderate body have general hexagon configurations. In some exemplary embodiments the dimension from a first side of the hexagon to a second side that is parallel to the first side (i.e., double the hexagon's apothem) of at least a substantial number of the hexagon shapes is about 0.35 mm. In some embodiments that dimension could be between about 0.02 mm to about 0.12 mm. The distance between hexagons (i.e., the distance from a first side of a first hexagon to a first side of a second hexagon, wherein the sides are parallel to one another and the hexagons are directly adjacent to one another) is about 0.05 mm, although this distance could be between about 0.01 mm and about 0.25 mm. The diameter of the moderate body can be about 3 mm, but in some embodiments it is between about 0.25 mm and about 13 mm. The above numerical limitations are merely exemplary and not intended to be limiting.

In some exemplary embodiments of the systems shown herein (e.g., those shown in FIGS. 4-11D), the minimal body is stainless steel, and is about 0.2 mm thick, except in the recess section. As shown in the figures, the openings in the minimal body each have general hexagon configurations. In some exemplary embodiments the dimension from a first side of the hexagon to a second side that is parallel to the first side (i.e., double the hexagon's apothem) of at least a substantial number of the hexagon shapes is about 1 mm. In some embodiments that dimension could be between about 0.1 mm to about 3 mm. The distance between hexagons (i.e., the distance from a first side of a first hexagon to a first side of a second hexagon, wherein the sides are parallel to one another and the hexagons are directly adjacent to one another) can be about 0.2 mm, although this distance could be between about 0.02 mm to about 0.12 mm. The diameter of the minimal body can be about 6.5 mm, but in some embodiments it is between about 3 mm and about 13 mm. The above numerical limitations are not intended to be limiting.

In some embodiments the diameter of the minimal body is at least about 2 times the diameter of the moderate body. In some embodiments the diameter of the minimal body is at least about 1.5 times the diameter of the moderate body. In some embodiments the size of the plurality of hexagons in the minimal body is at least about 2 times the size of the plurality of hexagons in the moderate body. In some embodiments they could be at least about 3 times, or at least about 4 times.

Figure 12:
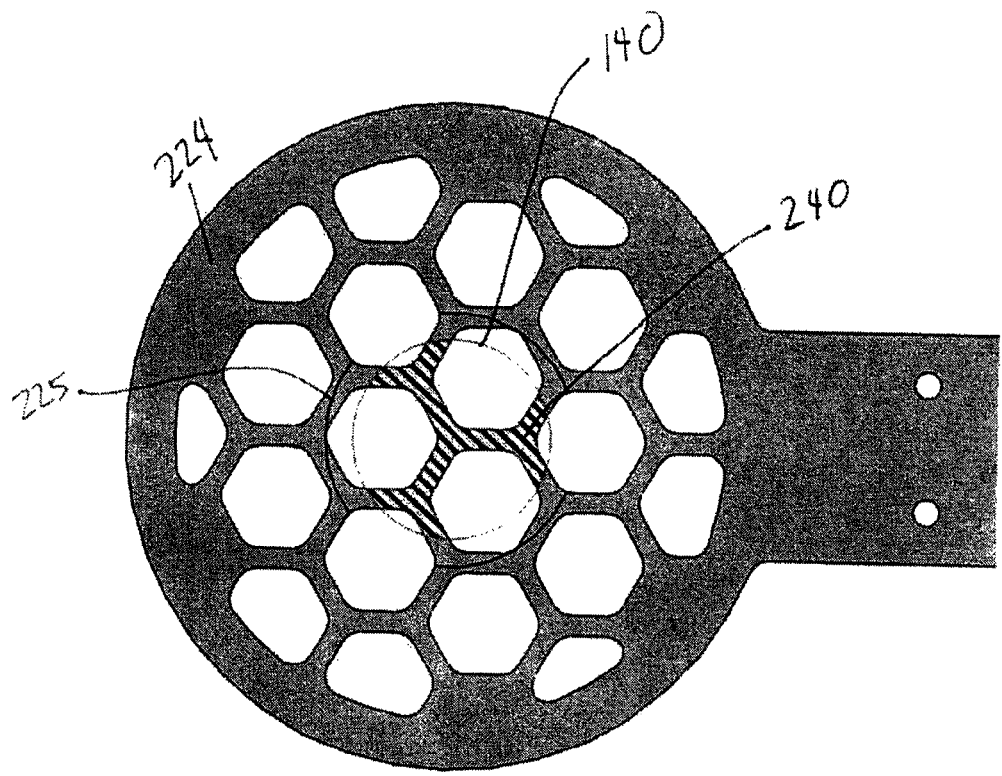
Figure 13:
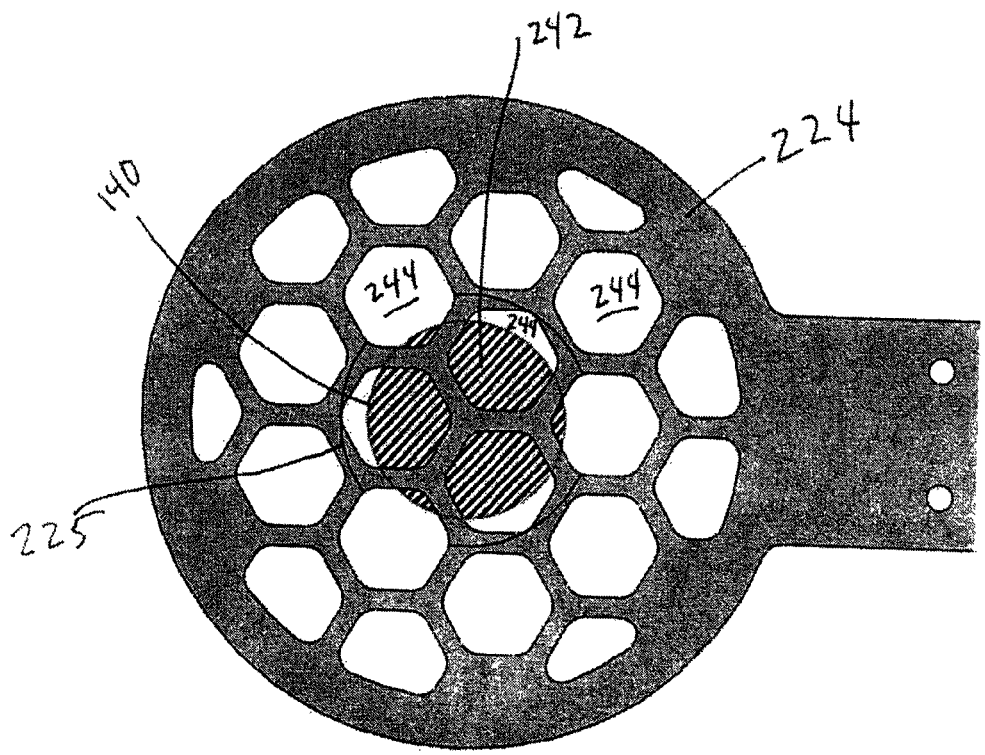

FIGS. 12-15 illustrate additional views illustrating the relative sizes and dimensions of the mesh bodies and a corneal inlay. In this embodiment the inlay has a diameter of about 2 mm. FIG. 12 is a top view illustrating minimal mesh body 224, recess 225 formed in minimal mesh body, periphery of inlay 140, and the surface area 240 (shown in hash lines) of minimal body 224 that overlaps with the inlay when the inlay is positioned in recess 225. In this particular embodiment surface area 240 of minimal body 224 that overlaps with the inlay is about 0.9 mm$^2$. The perimeter of the inlay that overlaps the minimal body is about 9 mm. FIG. 13 illustrates minimal mesh body 224 and periphery of inlay 140, and the surface area 242 (shown in hash lines) of openings 244 (only three openings 244 labeled) that overlaps the inlay when the inlay is in the recess. In this particular embodiment the surface area 242 is about 2 mm$^2$.

Figure 14:
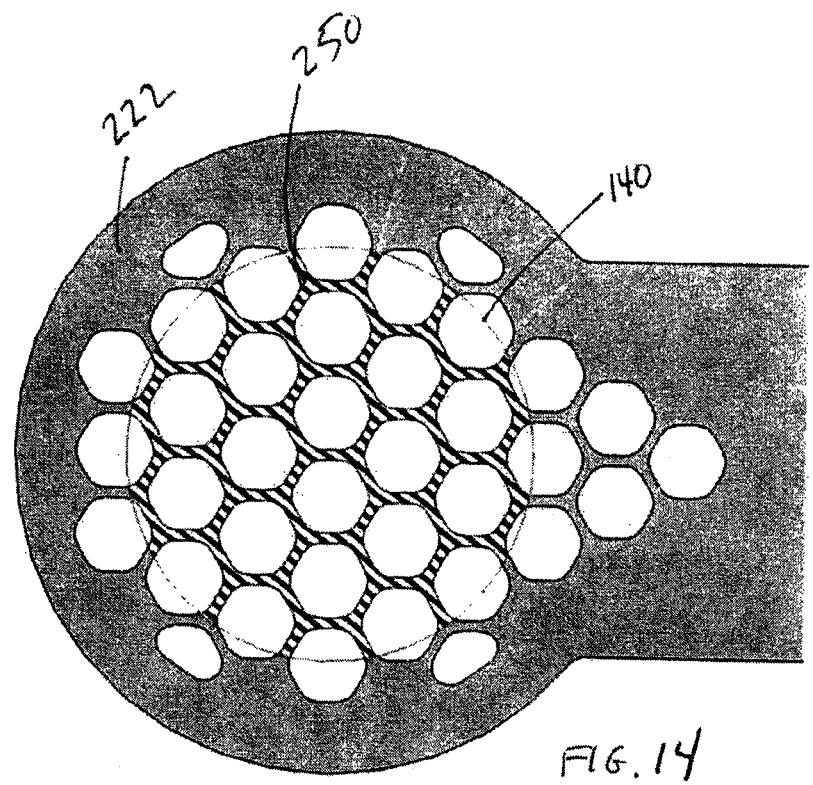
Figure 15:
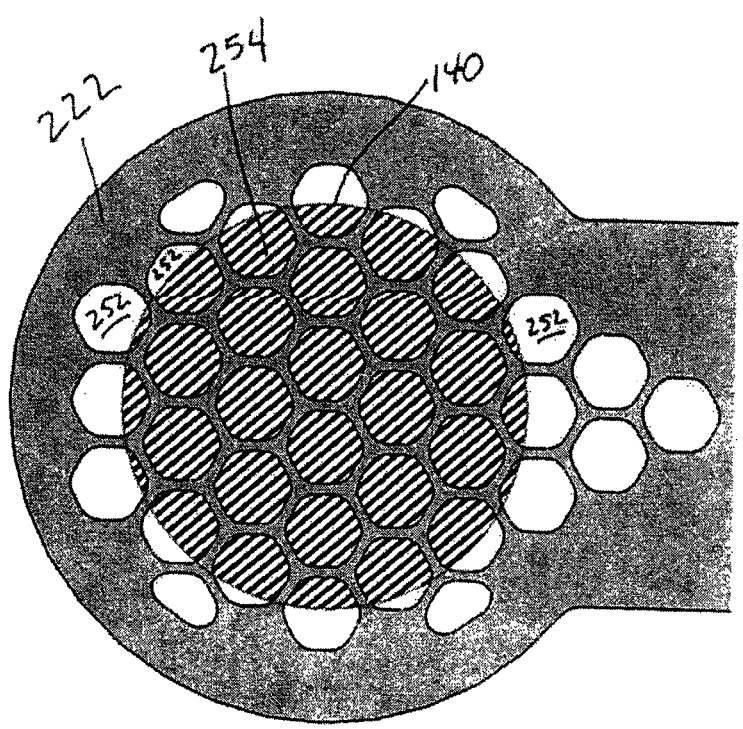
Figure 21I:
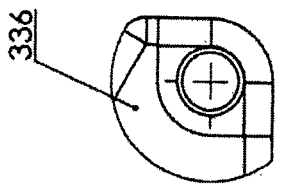
Figure 21H:
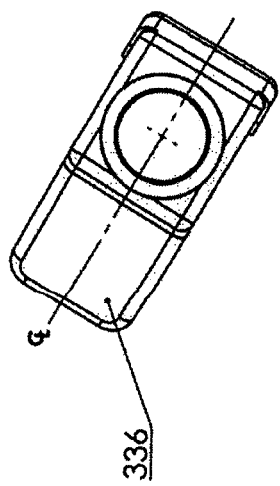
Figure 21G:
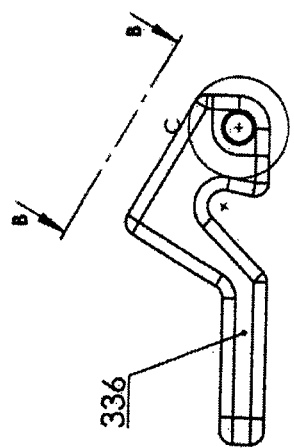
Figure 24D:
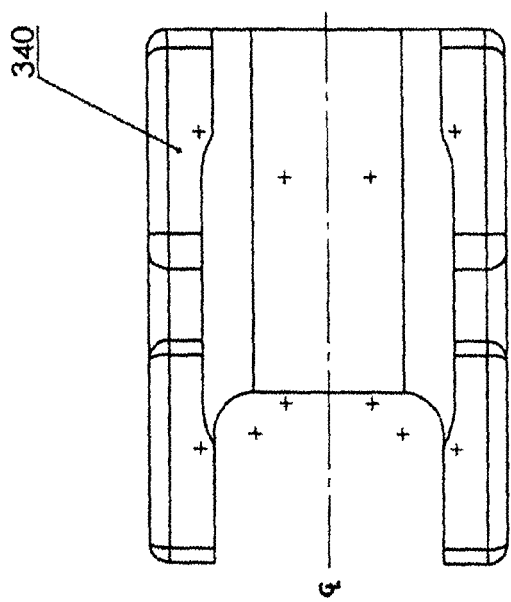

FIG. 14 illustrates moderate mesh body 222 and the periphery of inlay 140 disposed thereon. Surface area 250 of moderate body 222 is the surface area of the moderate body that overlaps the inlay, at least a portion of which is in contact with the inlay, when the inlay is positioned in the nest. In this particular embodiment surface area is about 0.75 mm$^2$. The perimeter of the inlay is about 26 mm. FIG. 15 illustrates moderate body 222, periphery of inlay 140, and the surface area 254 (shown in hash lines) of openings 252 (only three openings 252 are labeled) that overlap the inlay. Surface area 254 is about 2.3 mm$^2$.

In some embodiments the moderate body and the minimal body each have one or more openings, or apertures, extending through the bodies. The ratio of the moderate aperture perimeter (or sum of the aperture perimeters if more than one aperture) to the moderate aperture area (or sum of the apertures areas if more than one aperture) is greater than the ratio of the minimal aperture perimeter (or sum of the aperture perimeters if more than one aperture) to the minimal aperture area (or sum of the aperture areas if more than one aperture). Without necessarily wishing to be bound by a particular theory, the greater ratio results in greater forces being applied to the corneal implant from the moderate body than the minimal body, and thus provides the moderate body with a higher affinity for the corneal implant than the minimal body. When the moderate and minimal bodies are moved apart relative to one another, the greater forces applied to the implant will cause the implant to remain adhered to the moderate body rather than the minimal body.

By way of illustration only, in the embodiments shown in FIGS. 12-15, the sum of the perimeters of the apertures in the moderate body that overlap the implant were determined to be about 1.03 in, while the sum of the aperture areas that overlap the implant were determined to be about 0.0012 in$^2$. The ratio of perimeter to area for this particular moderate body was about 858 in$^{-1}$. The sum of the perimeters of the apertures in the minimal body that overlap the implant were determined to be about 0.365 in, while the sum of the aperture areas that overlap the implant were determined to be about 0.0014 in$^2$. The ratio of perimeter to area for this particular moderate body was about 260 in$^{-1}$. The ratio is therefore greater for the moderate body than for the minimal body.

FIG. 16 is a partial exploded view of an exemplary corneal implant storage and positioning device. Positioning device 310 generally includes a handle assembly 312 that includes the moderate body, support assembly 314 that includes the minimal body, and actuator assembly 316 that is adapted to actuate, or move, support assembly 314 with respect to handle assembly 312. Due to the inlay's greater affinity for the moderate body, the inlay will adhere to the moderate body when the support assembly 314 is actuated.

Actuator assembly 316 includes push rod 320 coupled to button 321, and spring 322. Handle assembly 312 includes handle 324 coupled to distal portion 326, which includes the moderate body. The distal end of spring 322 is secured within the internal channel within handle 312, and the proximal end of spring 322 is secured to the distal end of button 321. Push rod 320 is configured to be disposed within the internal lumen of spring 322. As shown in more detail in FIGS. 17A-17C, the distal end of push rod 320 includes bore 328 therethrough, adapted to receive dowel 318 therein. When push rod 320 has been advanced distally within handle assembly 312 and extends just out of the distal end of handle assembly 312, as shown in FIG. 17A, dowel 318 is advanced through bore 328. Dowel 318 both prevents push rod 320 from retracting proximally within handle assembly 312, but it also provides base assembly 314 with a surface to engage in order to secure support assembly 314 in place relative to handle assembly 312, as shown in FIG. 17C. The device also includes rod 330, which helps secure support assembly 314 in place relative to handle assembly 312 (see FIG. 17C), but allows support assembly 314 to rotate around rod 330 when the actuator is actuated. Dowel 318 is also involved in the actuation of the support assembly. Actuating button 321 causes push rod 320, and thus dowel 318, to be advanced distally within handle assembly 312. This causes dowel 318 to apply a generally distally directed force to support assembly 314, which causes dowel 318 to push down on support assembly 314. Upon the application of this force support assembly 314 will begin to rotate around rod 330, causing minimal body mesh 338 to move away from moderate mesh body 334. Further rotation of support assembly 314 will free support assembly 314 from rod 330, allowing support assembly 314 to be completely disengaged from handle assembly 312. Once disengaged, the corneal implant will remain adhered to moderate body 334 and is ready for use, such as delivery into or onto corneal tissue. Once the minimal mesh body is moved, the user can release button 321, and spring 322 causes actuator 316 to return to an at-rest, or non-actuated, position relative to handle assembly 312.

By incorporating rod 330, support assembly 314 rotates with respect to handle assembly 312 in only one direction, which prevents torqueing.

FIG. 18 is a partial exploded view of handle assembly 312 shown in FIG. 14 (actuator and base assembly not shown). Assembly 312 includes handle 324, distal tip portion 342, dowel 318, applicator base 336, and applicator 334. Handle 324 is secured to distal tip portion 342, and the distal end of distal tip portion 342 is disposed within a bore in applicator base 336. Applicator 334 is secured to applicator base 336. FIG. 19 shows the assembled view from FIG. 18.

FIGS. 20A-20D illustrate alternative views of the assembly of applicator base 336, applicator 334, and rod 330. FIG. 20A is an exploded perspective bottom view. FIG. 20B is a perspective top view illustrating how rod 330 is disposed within applicator base 336. FIG. 20C is a bottom view showing applicator 334 secured to applicator base 336 and a plurality of attachment points 350 for securing applicator 334 to applicator base 336. FIG. 20D is a front view showing applicator 34 secured to applicator base 336, and rod 330 disposed within applicator base 336. Applicator 334 and applicator base 336 can be secured together by any suitable technique. In one embodiment applicator 334 is welded to base 336, such as by resistance welding or laser welding. Applicator 334 includes the moderate mesh body.

FIGS. 21A-21I illustrate a variety of views of a particular embodiment of applicator base 336 described above. The internal bore through which the actuator extends can be seen in the sectional side view of FIG. 21D. The dimensions indicated in the figures are merely exemplary to this particular embodiment and are not limiting.

FIGS. 22A-22C illustrate exemplary dimensions for applicator 334, including the mesh dimensions, described above. For example, dimensions of the mesh that contribute to implant preference to adhere to the moderate body over the minimal body are shown. FIG. 22A is a top view. FIG. 22B is a side view. FIG. 22C is a detailed view of section A from FIG. 22A.

FIGS. 23A-23D illustrate support assembly 314 from FIG. 17, which includes support base 340 secured to implant support 338. Support base 340 and implant support 338 are secured to one another similarly to the applicator base and the applicator described above. FIG. 23A is an exploded view, while FIG. 23B is an assembled view. FIG. 23C is a top view. FIG. 23D is a detailed view C from FIG. 23A of applicator 338 showing recess 360 defined by recess sidewalls 356 and recess base surface 358. The implant is configured and sized to be disposed within the recess such that it is positioned between the minimal and moderate meshes prior to removal of the minimal body.

FIGS. 24A-24E illustrate front, sectional side, side, and top views of support base 340.

Figure 25A:
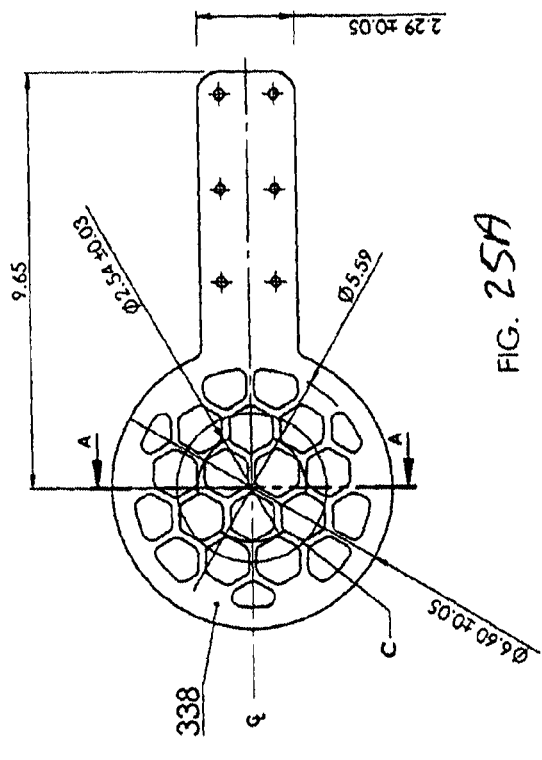
Figure 25C:
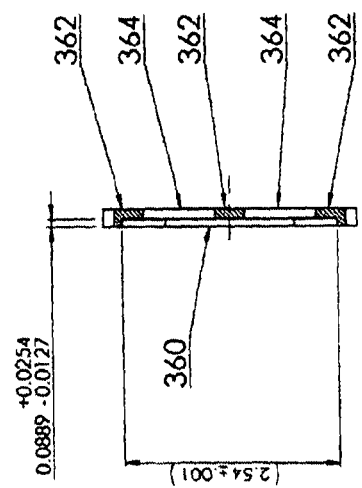
Figure 25B:
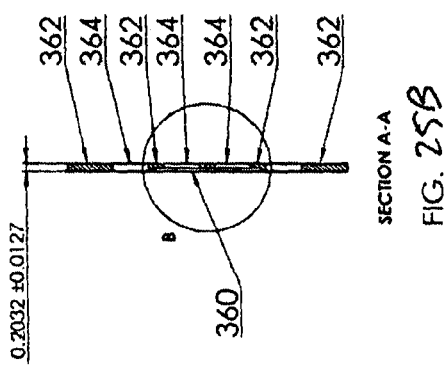
Figure 25D:
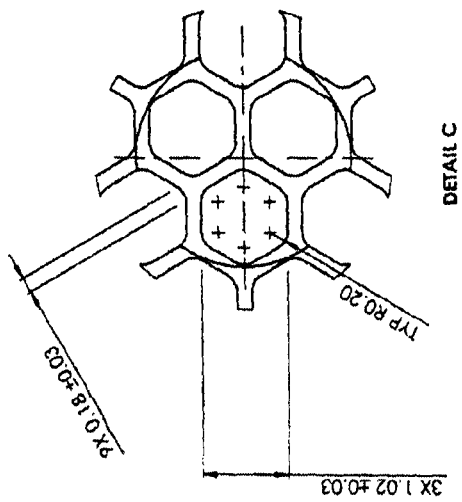

FIGS. 25A-25D illustrate views of the support 338. FIG. 25B illustrates section A-A shown in FIG. 25A. FIG. 25C shows detail B from FIG. 25B, and FIG. 25D shows detail C from FIG. 25A. Recess 360 is formed in a top portion of the support 338. Mesh apertures 364 are defined by body 362, illustrated in FIGS. 25B and 25C. The dimensions shown are exemplary and not intended to be limiting. The mesh apertures of the minimal body are larger than the mesh apertures of the moderate body, which is one of the contributing factors for why in this particular embodiment the implant preferentially adheres to the moderate body.

In general, the recess in the minimal mesh body should be sized to prevent forces, or a substantial amount of forces, from being applied to the corneal implant while it is positioned in the nest between the moderate and minimal bodies prior to use.

The mesh apertures and the recess can be created by any suitable technique, such as chemical etching, laser cutting, micro water jet cutting, etc. In some instances chemical etching provides for a cleaner cut and does not require as much post-manufacture processing of the body. The mesh apertures can be created from only one side, or in some embodiments half of the thickness of the aperture is created from one side, while the other half of the aperture is created from the other side. In some embodiments the recess is etched from one side, while the mesh apertures are created in the other side. Any combination or variation on these techniques can be used. In some embodiments the recess is created by plunge electrical discharge machining ("EDM").

In general, the net forces acting on the corneal implant are greater from the moderate mesh body than from the minimal mesh body. The polarity of water is an important factor when the corneal implant is formed of a hydrophilic material because in these instances the implant has properties like water and as such behaves like water. The dimensions of the mesh, configuration of the mesh, mesh body, and other factors can be modified to alter the relative affinities.

As described above, the minimal mesh body diameter is larger than the moderate mesh body diameter (both are shown to have a generally circular configuration). The minimal body diameter, due to its larger size, acts like a bumper, protecting the entire distal region of the apparatus during storage and use prior to actuation of the actuator. In the specific example shown above, the minimal body thickness is about twice as thick as the moderate body.

The moderate body diameter is larger than the recess, while the minimal body diameter is larger than the moderate body diameter. In some embodiments it may be helpful for the physician to be able to visualize the pupil when the corneal implant is being positioned in the cornea. For example, this may be desirable when implanting an inlay into the cornea wherein the inlay has a diameter less than the diameter of the pupil, such as a 1-3 mm diameter corneal inlay. For these applications the moderate mesh body can be sized such that it does not interfere with the visualization of the pupil. Specifically, the moderate mesh body portion is sized to allow the physician to be able to see the pupil during the delivery of the implant on corneal tissue. Starting with this constraint, the size of the other components can then be determined.

The use of "diameter" herein is not to suggest that the mesh body outer surfaces are perfectly circular or are circular at all. The two mesh portions could be square or rectangular-shaped, with the width and length of the minimal mesh portion larger than the width and length of the moderate mesh portion.

While in the embodiments above the implant's affinity for the moderate body is described as largely due to the size and configuration of the moderate mesh body relative to the minimal body, there are many ways to establish and control the implant's affinity for a given body. In some embodiments this can be accomplished by using a moderate body that is different than the minimal body. In some embodiments a finish could be applied to one or more of the surfaces of the moderate and minimal bodies. The finish can be different on the moderate and the minimal body to control the preferential adhesion. In some embodiments the moderate body has a better finish than the minimal body. In some embodiments the minimal body has a matte finish on it.

One or more components of the devices described herein can be a stainless steel or titanium. For example, applicator base 36 and applicator 34 can both be stainless steel, one can be titanium while the other is stainless steel, or both can be titanium.

Figure 26B:
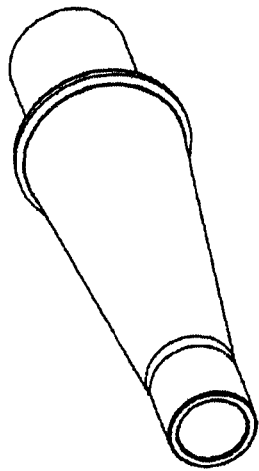
Figure 26C:
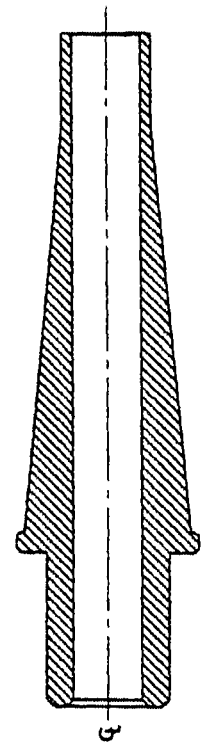
Figure 26A:
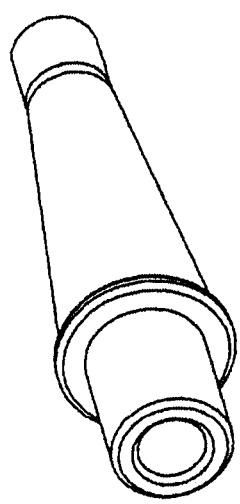
Figure 26D:
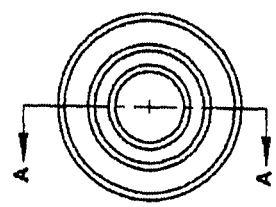

FIGS. 26A-26D illustrate views of distal tip 342 from the handle assembly described above. FIG. 26A is a view looking from the proximal end to the distal end, FIG. 26B is a view from the distal end to the proximal end, FIG. 26C is a sectional side view, and FIG. 26D is a front view. The distal tip is secured to the handle, and the distal end of it is disposed in the applicator base 336.

Figure 27D:
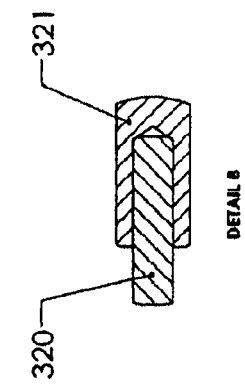
Figure 27E:
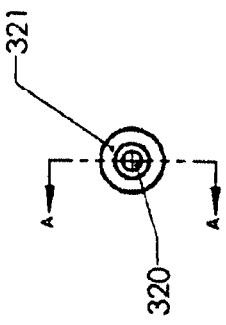
Figure 27C:
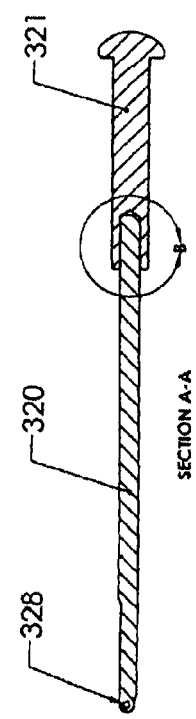
Figure 27B:
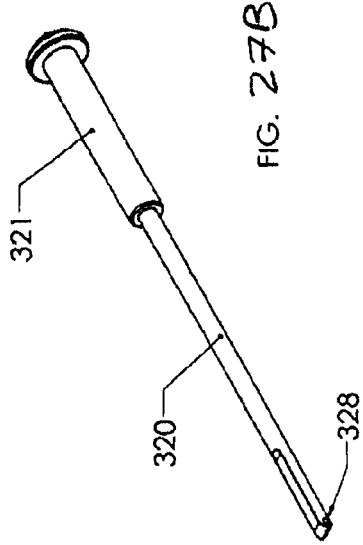
Figure 27A:
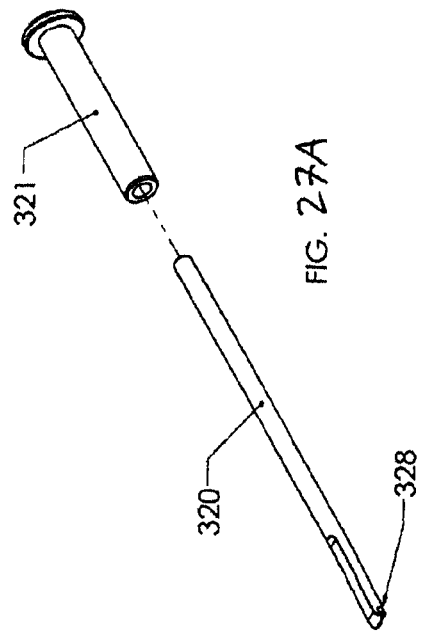
Figure 28B:
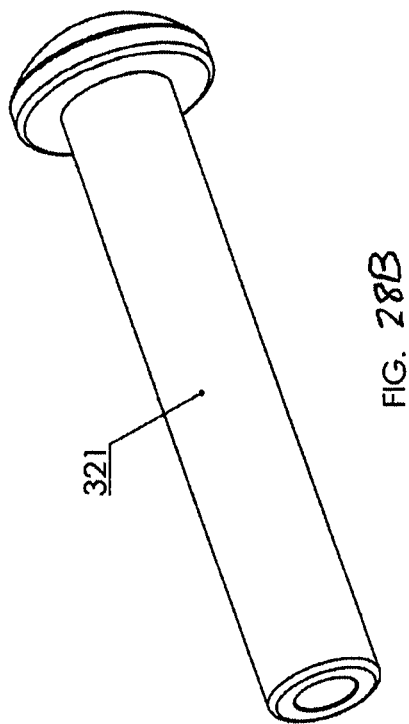
Figure 28A:
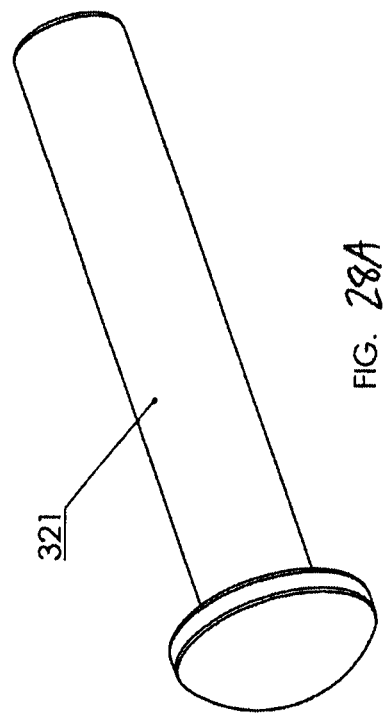
Figure 28D:
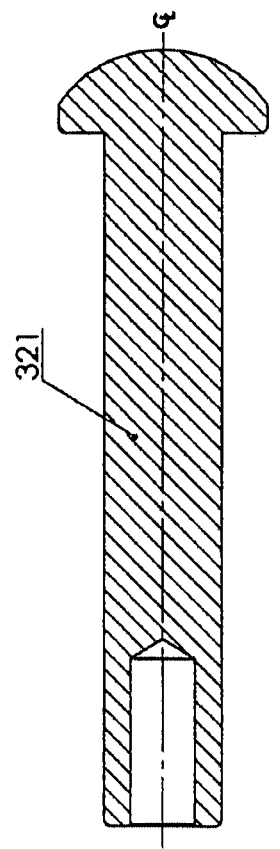
Figure 28C:
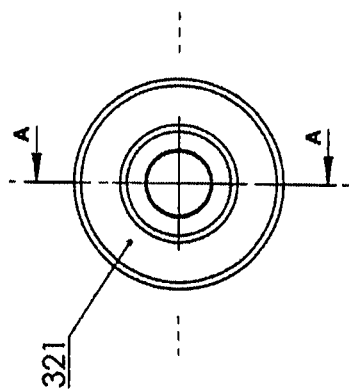
Figure 29A:
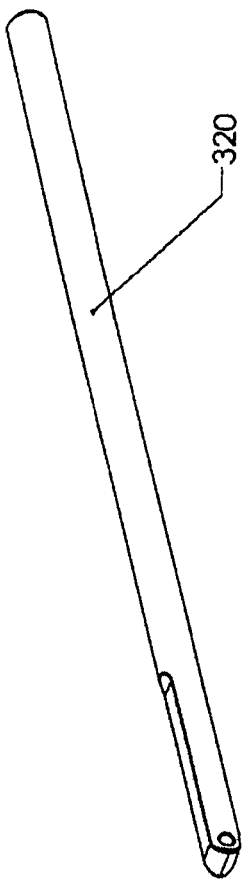
Figure 29B:
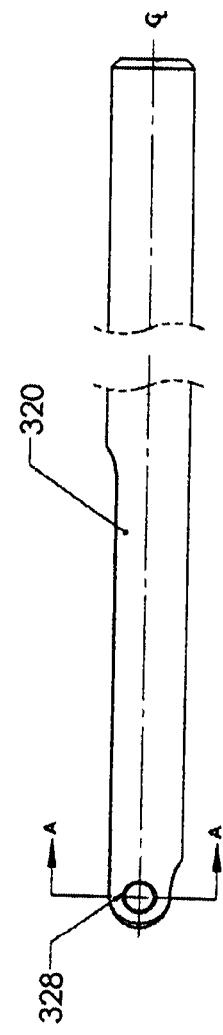
Figure 29C:
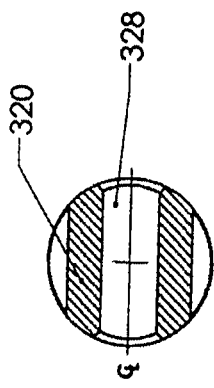
Figure 29D:
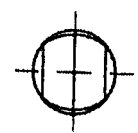

FIGS. 27A-27E illustrate in detail actuator assembly 316 from FIG. 16. The actuator includes button 321, push rod 320, and bore 328 at the distal end of push rod 320. FIG. 27A is an exploded view, FIG. 27B is an assembly view, FIG. 27C is a side sectional view of section A-A shown in FIG. 27E, and FIG. 27D is a detail view of section B shown in FIG. 27C.

FIGS. 28A-28D illustrate detailed views of button 321. FIGS. 29A-29D illustrate detailed views of push rod 320, including bore 328.

Figure 31A:
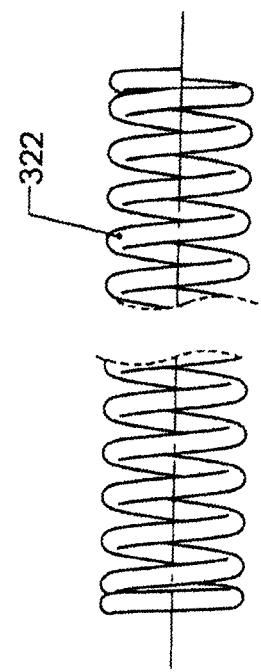
Figure 31B:
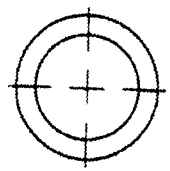
Figure 32A:
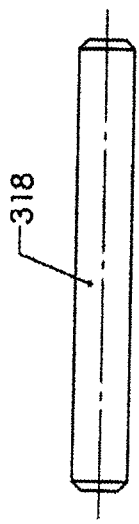
Figure 32B:
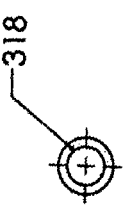

FIGS. 30A-30D illustrate detailed views of handle 324. FIGS. 31A and 31B illustrate detailed views of spring 322. FIGS. 32A and 32B illustrate detailed viewed of dowel 18.

Once the corneal implant is loaded in the apparatus between the moderate and minimal bodies, the implant can be used right away or it can be stored in packaging for any suitable period of time. When the corneal implant is made of a hydrogel material, it is important to keep the implant adequately hydrated during storage.

The following disclosure describes packaging tools and assemblies that are adapted to keep the corneal implant adequately hydrated during storage. As set forth in more detail below, the following embodiments can also remove excess fluid from the portion of the implant applicator apparatus in which the implant is disposed. Removing excess fluid helps ensure that when the minimal body is removed, the corneal implant will adhere to the moderate body.

The packaging tools and assemblies described herein generally provide one or more of three important functions: 1) to surround and protect the applicator apparatus, including the corneal implant retained therein, from damage; 2) to act as a fluid reservoir and provide fluid to the corneal implant to keep the corneal implant hydrated during storage; and 3) to remove, or wick away, excess fluid when removing the corneal implant applicator from the packaging materials.

FIGS. 33A (side view) and 33B (top view) illustrate an exemplary packaging assembly 400 with corneal implant applicator apparatus 402 disposed therein. Assembly 400 includes housing, or tray, 404, and lid 406. Housing 404 includes a distal reservoir, or well, 420, which is adapted to accommodate the distal end of applicator apparatus 402 (in which the corneal implant is disposed) and hydration control member 408. Hydration control member 408 is disposed within reservoir 420, and is positioned within reservoir 420 such that it interacts with the portion of the apparatus 402 in which the corneal implant is disposed. In this embodiment hydration control member 420 is a porous bag filled with a hydrogel material. The hydrogel material acts like a liquid reservoir, and the pores are sized to allow fluid molecules to pass through the pores. The bag is folded upon itself at folds 414, forming three bag sections 412. Two of the sections form a passage, or pocket, that is adapted to receive the portion of apparatus 402 in which the corneal implant is disposed. In particular, in this embodiment, the apparatus 402 is the apparatus from FIG. 16. The moderate mesh and minimal mesh (with implant therein) are positioned within the passage formed between two of the sections of bag, as shown in the figure. The moderate mesh and minimal mesh engage the two sections of the bag. The two sections form a passage into which the relatively thin moderate/minimal body assembly can be disposed. When the distal end of apparatus 402 is positioned within the passage of hydration control member 420, the corneal implant, due to the openings in the moderate and minimal mesh bodies and the pores in the bag, is in fluid communication with the hydrogel material in the bag. The hydrogel material (or other hydrophilic material) within the bag keeps the corneal implant hydrated during storage in the packaging. In use, when apparatus 402 is removed from the passage formed by the two sections of the porous bag, the sections of the bag wick away excess storage fluid that adheres to the moderate body and minimal body. This prevents too much storage fluid from remaining adhered to the moderate and minimal bodies when prepping the implant to be deposited onto corneal tissue.

In general, the hydration control element helps keep the corneal implant hydrated during storage. This is of particular relevance when the implant is made at least partially from a hydrophilic material such as a hydrogel. The hydration control element generally acts like a fluid reservoir that is in fluid communication with the corneal implant via the openings in the moderate and minimal mesh bodies.

Figure 35:
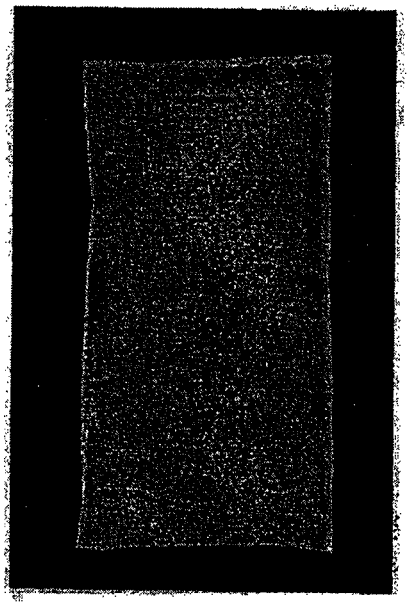
FIGS. 34-36B illustrate exemplary hydration control members.
Figure 34:
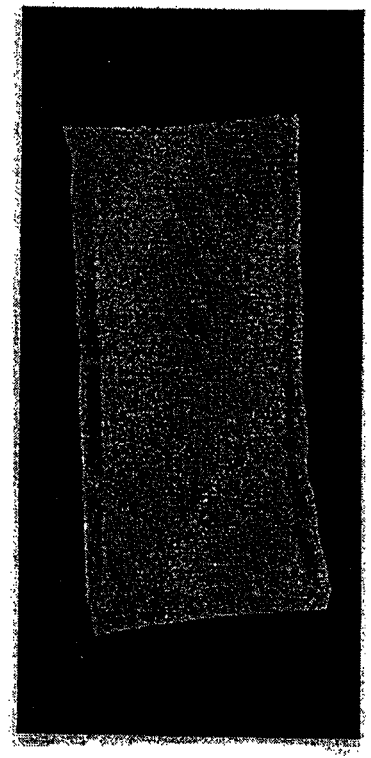

FIG. 34 illustrates a hydration control member in the form of a porous bag filled with a hydrogel material. FIG. 35 illustrates a hydration control member in the form of a porous bag filled with glass beads. The glass beads within porous bag provide the same hydration to the implant as does the hydrogel material within the bag from FIG. 34.

The porous bag is adapted to maintain an equilibrium, or substantial equilibrium, with the nest within the moderate and minimal bodies. This provides enough fluid to the implant to keep the implant hydrated during storage. The bag can be a polyester material or any other suitable material. In some embodiments the bag is polyether ether-ketone ("PEEK"). The bag pore size is sized to prevent particulates from leaking out of the bag and to control the hydration of the corneal implant. In some embodiments the bag mesh size is between about 10 microns and about 50 microns. In some embodiments the pore size is about 30 microns. If hydrogel is used within the bag, the hydrogel material can be medical grade or non-medical grade.

Figure 36A:
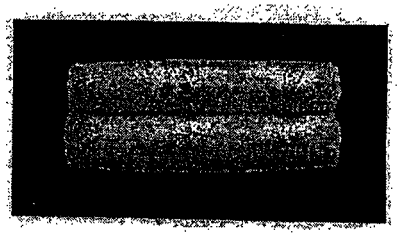
Figure 36B:
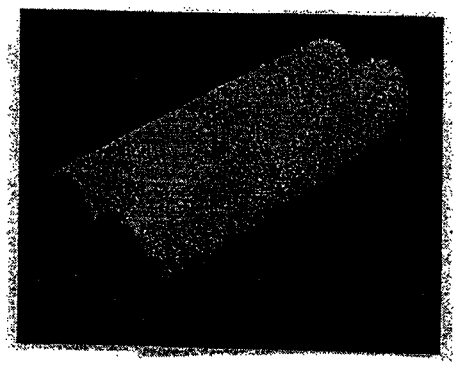

In an alternative embodiment the hydration control member comprises two hydration control elements that are rolls of material that form a pocket, or passage, therebetween. FIGS. 36A and 36B illustrate an exemplary hydration control member that comprises two rolls of a polyester mesh material that form a pocket therebetween. The two rolls are first and second hydration control elements. The pocket formed by the two rolls is adapted to receive the portion corneal implant applicator apparatus that houses the corneal implant. In this embodiment the two rolls are formed from a single piece of material that is rolled up like a scroll to form first and second hydration control elements.

Figure 37A:
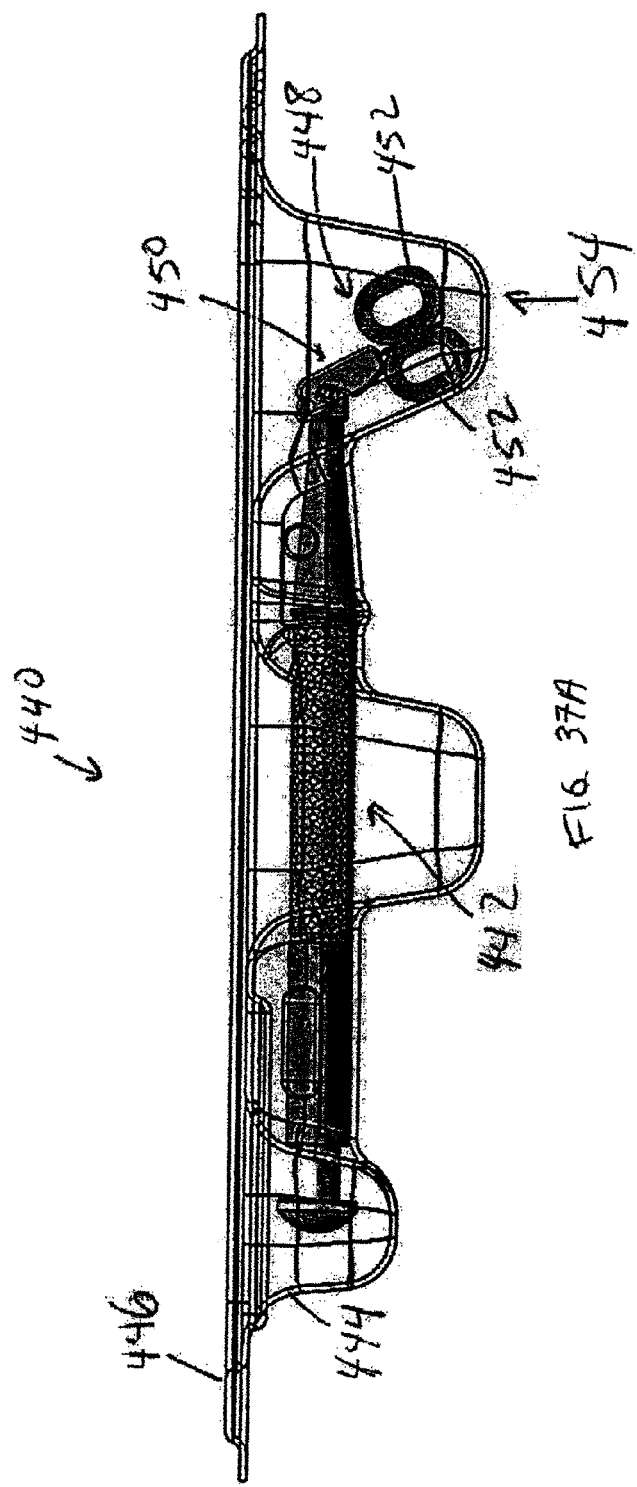

FIGS. 37A and 37B illustrate packaging assembly 440 wherein the hydration control member 448 comprises the two rolls of material (e.g., a polyester material) from FIGS. 36A and 36B. Corneal implant applicator apparatus 442 is the apparatus shown in FIG. 16. The packaging 440 includes tray 444 and lid 446. Tray 444 includes reservoir 454 in which the distal end of apparatus 442 is positioned. The two rolled hydration control elements of hydration control member 448 form a pocket, or passage, therebetween. The pocket is adapted to receive and stabilize the moderate and minimal bodies therein. In this embodiment the two rolls of material are in contact with each other, and the pocket is the general wedge configuration defined by the outer surfaces of the two rolled sections. When the distal end of apparatus 442 is advanced into the pocket, the distal end of the apparatus pushes the rolls apart slightly. The distal end of the apparatus is advanced to a position in which the two rolls are disposed on either side of the corneal implant (which is disposed within the nest) and are in contact with the minimal body and the moderate body, respectively. The rolled elements are therefore in fluid communication with the corneal implant via the openings in the moderate and minimal bodies.

The hydration control member also stabilizes the moderate and minimal bodies (and the implant disposed in the nest) when the distal end of the apparatus is disposed in the pocket. When the apparatus is advanced into the pocket, the hydration control member engages with and stabilizes the moderate and minimal bodies in the packaging. This prevents the distal end from jostling around and possibly being damaged while in the packaging. "Stabilize" as used herein means that the distal end of the apparatus is more stable than it would be without the presence of the hydration control member. The distal end need not be completely immobilized to be stabilized, but it is generally preferred that the distal end doesn't move relative to the hydration control member.

In alternative embodiments the first and second hydration control elements are not material that is rolled up, but are rather cylindrically-shaped solid material. The two elements would either be secured within the tray, or they could be secured to a base member.

One of the advantages of the hydration control member is that it is adapted to wick away, or strip, excess fluid from the moderate and minimal bodies when the apparatus is removed from the pocket. This is in part because the two hydration control elements are in contact with the moderate and minimal bodies as they are removed from the pocket. The hydration control elements act in some ways like two squeegees to strip away excess fluid as the distal end is removed from the pocket. When stripping away the excess fluid the hydration control elements do not necessary absorb the excess fluid, but rather simply strip it away from the moderate and minimal bodies. This can be advantageous because even if the hydration control elements are substantially saturated with fluid, they can still remove the excess fluid from the moderate and minimal bodies. In some particular embodiments it has been found that between about 0.5 and about 1.5 microliters is an optimal amount of fluid associated with the moderate body and minimal body after the wicking step. That amount of fluid is partially controlled by the wicking away of the fluid during the removal process. The amount of fluid that remains with the inlay is also a function of the moderate mesh body thickness (about 0.1 mm nominal) and the opening pattern of the mesh.

In embodiments in which a bag is part of the hydration control member, the hydration device need not be folded or formed in any specific configuration. For example, a bag could simply be deformed in such a way that the distal end of the apparatus will maintain substantial contact with the hydration control member. Additionally, the hydration control member could be engaged with only one side of the distal end of the apparatus and the apparatus could still be stable and the excess fluid could still be removed.

Figure 38A:
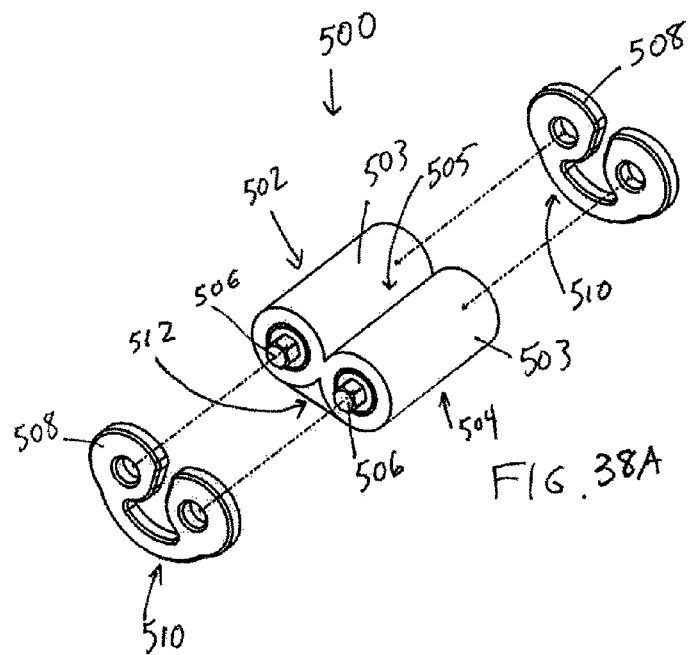
Figure 38B:
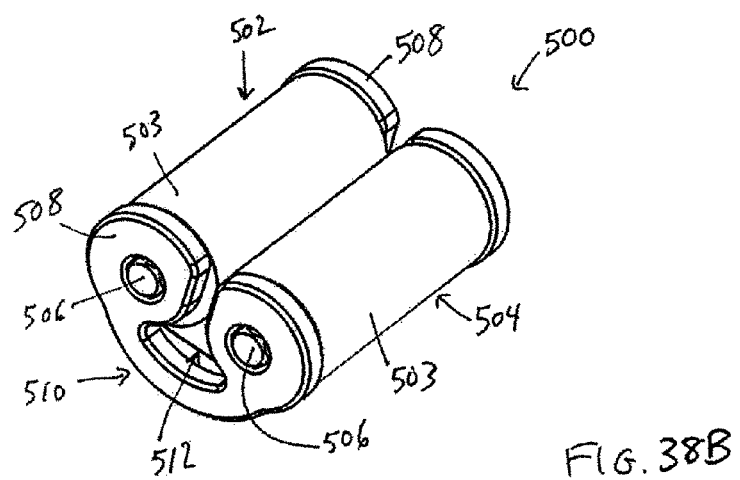

FIGS. 38A-40B illustrate an alternative embodiment of a hydration control member. Hydration control member 500 includes first hydration control element 502 and second hydration control element 504, cores 506, and two deformable bases 508. FIG. 38A shows an exploded view while FIG. 38B shows the assembled view.

Hydration control elements 502 and 504 are formed by rolling up a single piece of material 503 around cores 506 to form two rolled sections, similar to a scroll. To form the scrolls, ends 501 of material 503 are passed through slits in cores 506, as shown in FIG. 40A, and then rolled back around core 506 as shown in FIG. 40B. Cores 506 are then rolled up over material 503, which rolls material around cores 506. The two cores 506 are rolled up in opposite directions until they engage. They are rolled up so that hydration elements 502 and 504 have substantially the same amount of material 503 in them. The material and cores after being rolled up are shown in the central exploded illustration in FIG. 38A. Pocket 505 is formed by the surfaces of hydration control elements 502 and 504.

In some embodiments the cores are PEEK, but can be any other suitable material, such as a polyester material.

The material forming the hydration control elements preferably has water wicking properties. These properties help remove the excess fluid from the apparatus. Exemplary suitable materials include woven fabric polyester materials. The wicking properties of the hydration control elements also help ensure hydration of the inlay when in the packaging. Any loose water (i.e., condensate) in the packaging that comes into contact with the hydration control elements will be wicked up and made available to the corneal implant due to the fluid communication with the implant via the openings in the moderate and/or minimal bodies. This can be highly advantageous if the packaging assembly goes through a steam sterilization cycle, for example, as there will likely be condensate present in the packaging at the end of the cycle.

Hydration control member 500 also includes two deformable bases 508 which are secured to the ends of cores 506. Bases 508 each have two bores through them that are adapted to receive an end of cores 506. Bases 508 have spring-like properties so that they can be slightly deformed when the distal end of the applicator is advanced through the pocket. In this embodiment bases 508 include living hinges 510, which allow for the slight deformation of bases 508. When the applicator is advanced into pocket 505, the general C-shaped bases 508 are opened slightly, due to the living hinge, to accommodate the implant applicator apparatus. In this slightly deformed configuration, the hydration control elements 502 and 504 are each pressing on the moderate and minimal mesh bodies, helping stabilize the applicator apparatus in the pocket.

If the bases 508 are intended to be able to accommodate a greater degree of separation of cores 506, bases 508 can be modified to provide a greater degree of deformation. For example, the bases 508 could include a hinge formed of two materials, which may provide a greater degree of movement than living hinges 510. Bases 508 could also be formed of a material with superelastic properties such as nitinol.

Once the cores 506 are secured to bases 508, hydration control member 500 can be placed within the packaging, and the distal end of the apparatus can be advanced into the pocket.

When the hydration control elements 502 and 504 are formed from a single piece of material in this manner, backstop 512 is formed that is substantially in the center along the length of material 503. The backstop is situated at the back of the pocket and prevents the distal end of the apparatus from being advanced too far into the pocket. In this embodiment the applicator is advanced into the pocket such that the inlay is positioned just distal to where the hydration control elements engage each other, so that when the apparatus is removed from the pocket, the excess fluid can be properly wicked away from the distal end of the applicator apparatus. The corneal implant can also be disposed where the two hydration control elements meet, or it can be disposed closer to the backstop.

Alternatively, hydration control member 500 can simply be used as a temporary hydration device and need not be positioned within a packaging container. For example, a user could simply keep the distal end of the implant applicator apparatus disposed within the hydration control member pocket to keep the implant hydrated.

Figure 33B:
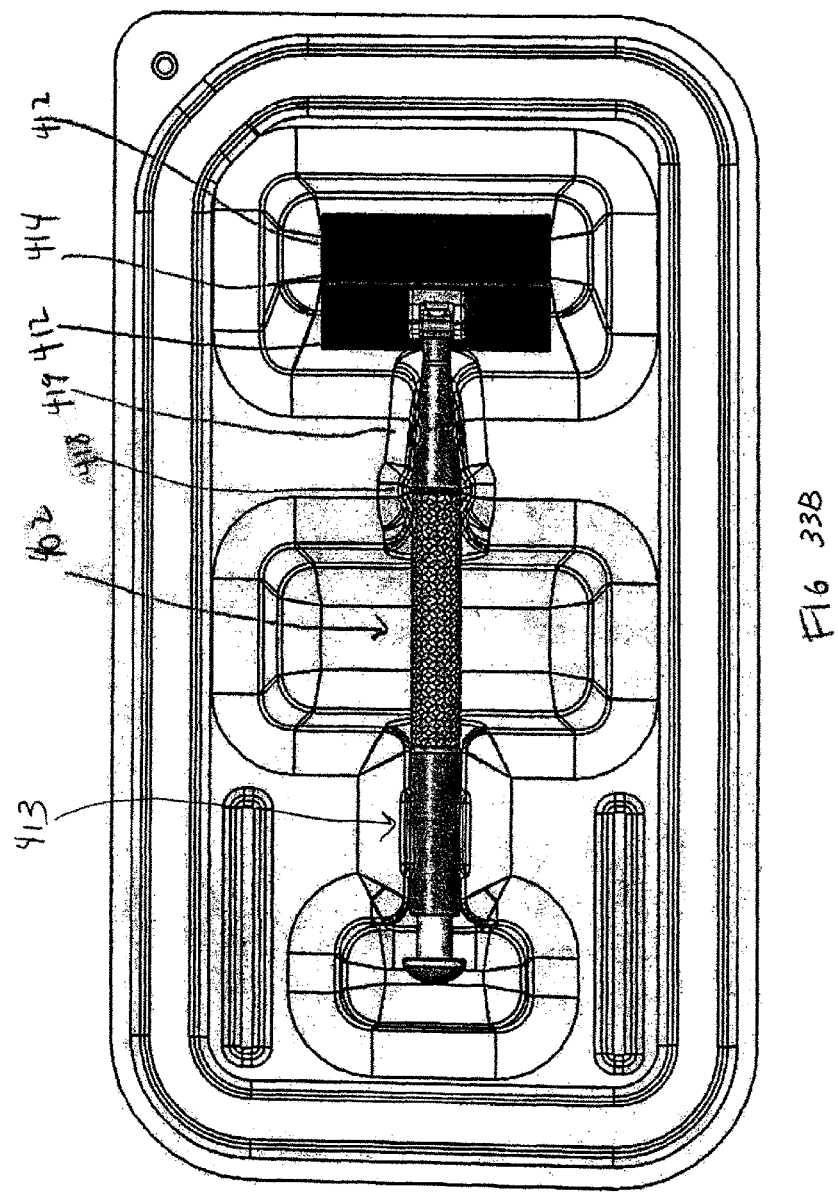

In some embodiments the tray includes snap features adapted to engage and stabilize the implant applicator apparatus during storage to prevent or minimize movement in the tray. The snap features can be disposed on a distal portion of the tray, a proximal portion of the tray, or both. In the distal portion they grab onto and secure a distal portion of the apparatus. If in a proximal region the snap features are adapted to secure a proximal region of the apparatus. Exemplary distal snap features that are formed into the tray and are adapted to securingly engage with a distal portion of the apparatus are shown in FIG. 33B as elements 418 and 419. Exemplary proximal snap feature 413 is adapted to stabilize the proximal portion of the apparatus. In the distal portion they may face less resistance than they would face if they were disposed in the proximal portion and grab onto the proximal portion of the device. In this embodiment the tray can include proximal snap features 413 but does not include the distal snap features. In embodiments in which the packaging only includes proximal snap features, the snap features can provide a location around which the apparatus pivots as the apparatus is removed from the packaging. An exemplary benefit of this type of motion when proximal snap features are included rather than distal snap features is that the distal end of the apparatus, which includes the implant nest, can be removed from the pocket with less risk of disassociation of the moderate and minimal bodies, and provides for better wicking of excess fluid as the corneal nest is removed from the pocket. This type of relative motion also reduces the likelihood of any damage to either the moderate or minimal bodies during the removal step.

Figure 41A:
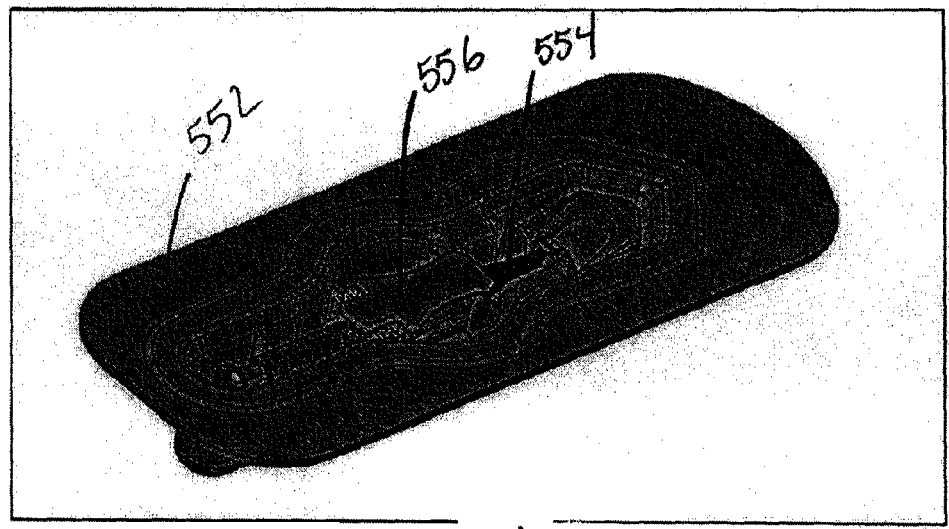
FIGS. 41A-41E illustrate an exemplary packaging apparatus.
Figure 41B:
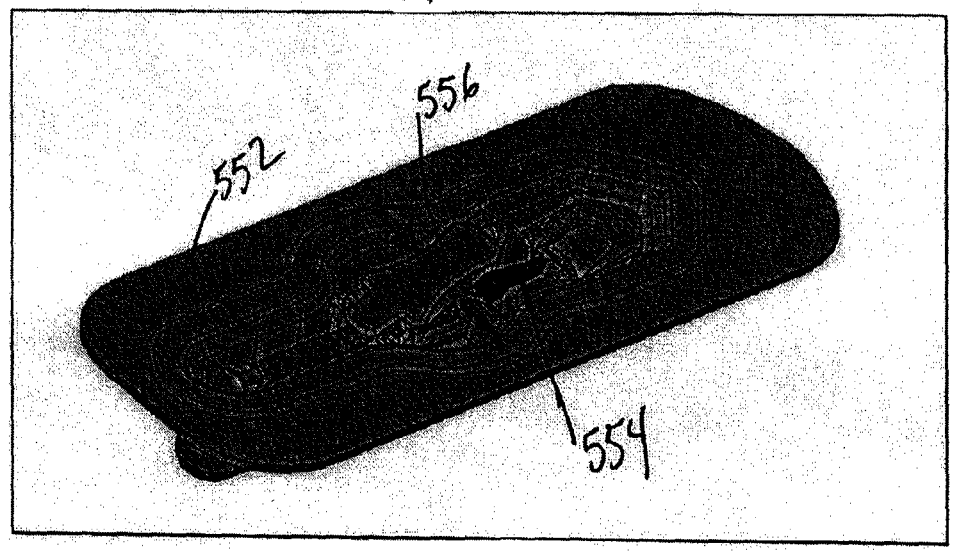
Figure 41C:
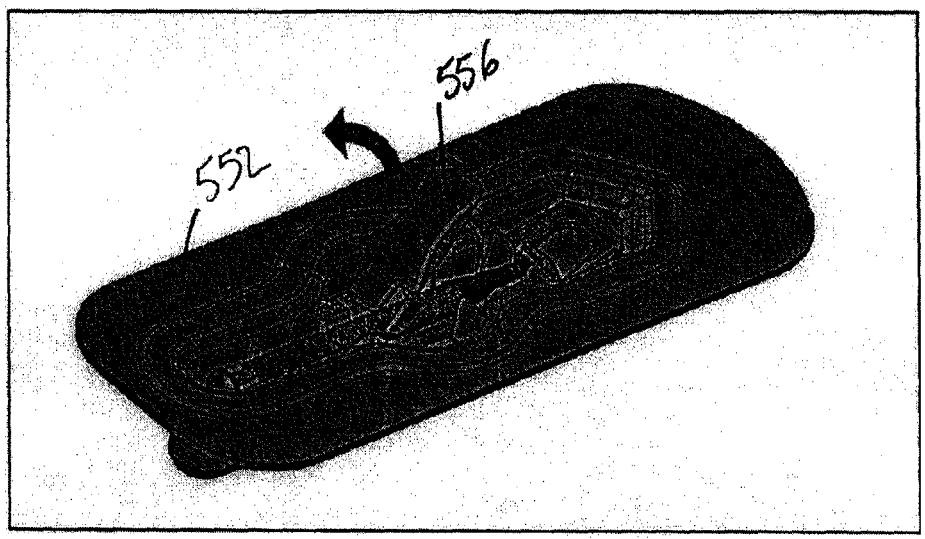
Figure 41D:
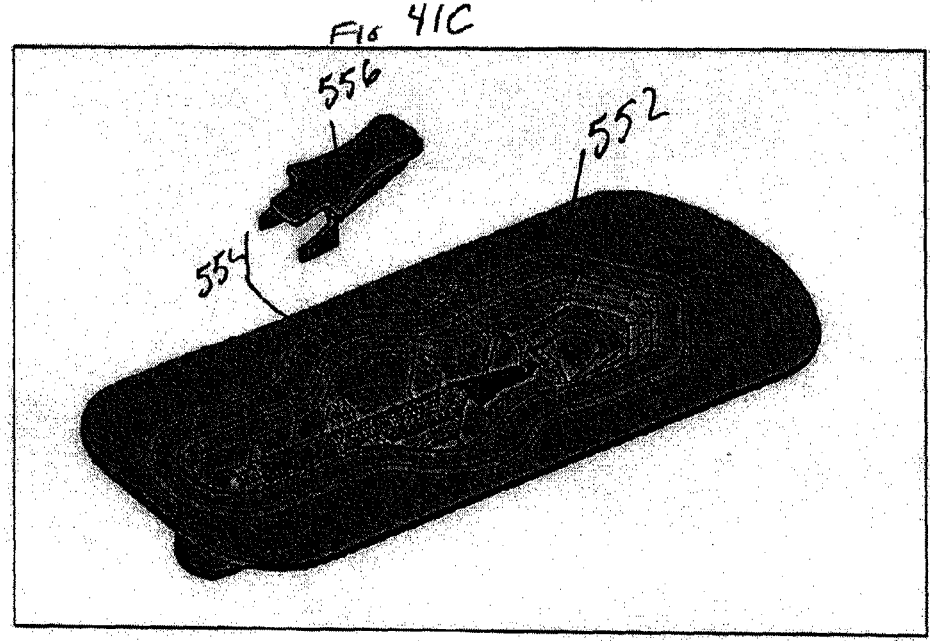
Figure 41E:
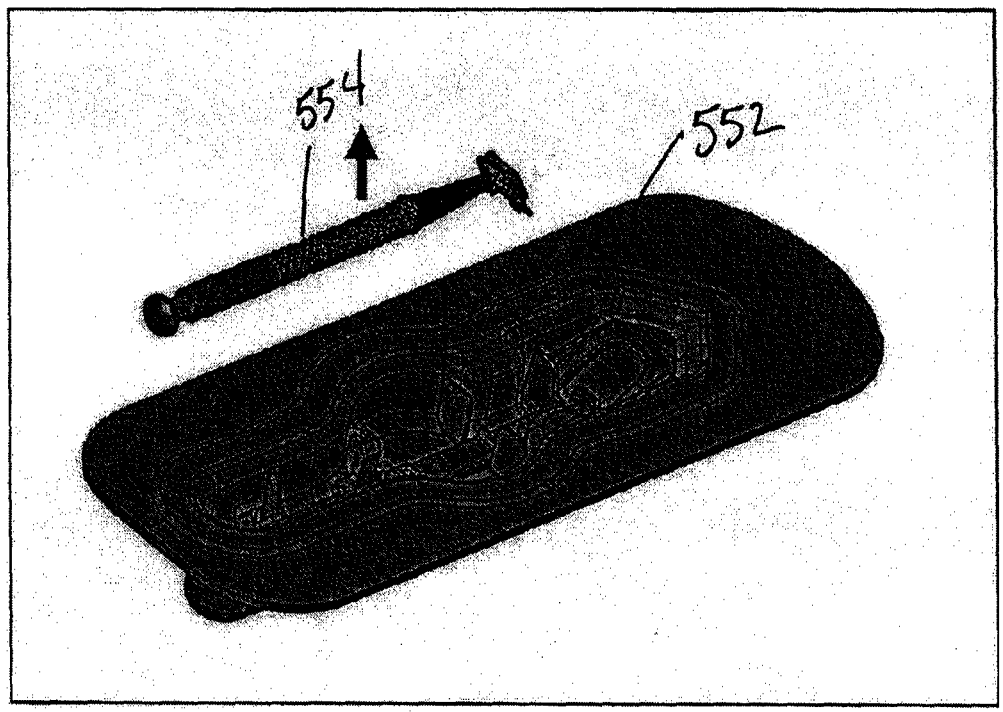

FIGS. 41A-41E illustrate an embodiment of an exemplary packaging tray 552 (lid not shown) including a lock 556 and a method of removing corneal implant applicator 554 from the packaging tray. Lock 556 helps stabilize apparatus 554 within tray 552, in particular the handle portion of the apparatus. In FIG. 41A, the lid has already been removed. In FIG. 41B, the sides of lock 556 are depressed in the direction of the two arrows and the lock is lifted up away from apparatus 554. After the lock has cleared locking elements in the tray, lock 556 is fully disengaged from the tray, as shown in FIGS. 41C and 41D. Once the lock is removed apparatus 554 is removed from tray 552, as shown in FIG. 41E. A hydration control member is not shown in FIGS. 41A-41E, but any of the hydration control members described herein can be included in the well, or reservoir, in the tray. The lock and the tray can also be made to be an integral structure rather than being separate components.

The tray lid and housing preferably do not include any leachable materials, as the implant may be stored in the packaging for any length of time, including several years. Additionally, the packaging material, including the tray, should be autoclavable for sterilization. The tray can be thermoformed, injection molded, or formed by other suitable methods. In one particular embodiment the tray is a TOPAS® COC material, such as COC6015. The tray can also be formed from polypropylene or other plastic materials.

As set forth above one or more components of the device can be made from a variety of materials. For example, one or more components can be stainless steel, and one or more components can be titanium. Titanium is more corrosion resistant than stainless steel and thus may be a better material when the materials are exposed to water. When stainless steel components are used, one or more treatments can be applied to the stainless steel, such as to make them more resistant to corrosion. In some embodiments the parts are passivated, while in some embodiments the parts are coated with a zirconium nitride coating. In some embodiments the parts are both passivated and coated with zirconium nitride. In a particular embodiment one or more components are 316L stainless steel. A zirconium nitride coating can also be used to make the components harder to make them stiffer and more protective. For example, a zirconium nitride coating can be applied even if titanium were to be used as the material. In some embodiments the moderate and/or minimal mesh bodies, or any other component of the apparatus, could be a plastic material. This could make the apparatus cheaper if it or portions of it are intended to be disposable.

In some embodiments the assembled packaging (tray, lid, and applicator apparatus disposed therein) needs to be sterilized. In some embodiments it is sterilized by autoclaving. Due to the water in the corneal implant, the water associated with the hydration control member, autoclaving creates steam within the sealed tray. The internal pressure after autoclaving can get as high as 350 kPa or higher. The tray should be able to withstand the internal pressure increase, and the seal between the lid and the tray needs to be able to withstand the internal pressure increase. If the seal between the lid and tray breaks, the inside of the packaging is no longer a sterile environment.

Additionally, as set forth above, the relative size of the minimal mesh body provides protection for the moderate mesh body during packaging and removal. This is because the diameter of the minimal mesh is greater than the diameter of the moderate body, and because the minimal mesh body has a greater thickness than the moderate body. In some of the embodiments herein, the minimal body is about twice as thick as the moderate body (except for the portion in which the recess is created).

In some embodiments the handle, such as handle 324 in FIG. 16 is an injection molded plastic handle. It can be desirable to have a knurl pattern on it to improve the physician's tactile feel. Some knurl patterns are, however, difficult to clean. Additionally, the pattern can wear away on the packaging materials during storage. In some embodiments the handle has one or more spiral patterns that make it smoother, which makes it wear less on the packaging material.

The storage and/or positioning devices described herein can be used to store and/or position corneal inlays such as those exemplary inlays described in U.S. Pat. No. 6,102,946, filed Dec. 23, 1998, application. Ser. No. 11/106,983, filed Apr. 15, 2005, application Ser. No. 10/837,402, filed Apr. 30, 2004, application Ser. No. 11/554,544, filed Oct. 30, 2006, Provisional Application No. 60/776,458, filed Feb. 24, 2006, application Ser. No. 12/418,325, filed Apr. 3, 2009, application Ser. No. 11/738,349, filed Apr. 20, 2007, application Ser. No. 12/877,799, filed Sep. 8, 2010.

When the minimal body is moved relative to the moderate body, an amount of fluid remains adhered to the corneal implant and the moderate body due to adhesive forces between the fluid and the implant, and between the fluid and the moderate body. This is generally referred to as the amount of fluid that is left behind after separation of the moderate and minimal bodies. In some particular embodiments it has been found that between about 0.5 and about 1.5 microliters is an optimal amount of fluid that is left behind. This amount is not intended to be limiting. As set forth above, the pivoting motion of the minimal body relative to the moderate body helps ensure that the amount of fluid that remains is desirable.

The disclosure that follows generally describes devices and methods for moving a corneal implant, or other hydrophilic implant, from one location to another location. The devices and methods utilize the property of surface tension to control the inlay. The devices can be used to pick up the implant from one surface or material and deposit it onto a second surface or material. In some embodiments above, the corneal implant is positioned in a recess in the minimal mesh body. The disclosure that follows describes exemplary devices and methods of depositing the corneal implant into the recess of the minimal mesh body of the devices above.

As is shown above with respect to FIG. 42, in the case of liquid suspended within a loop, adhesion forces act on both the top and bottom surfaces and cohesive forces throughout both surfaces. These forces are sufficient to hold a liquid within a loop up until the liquid's volume is such that the gravitational forces overcome the adhesion forces.

Figure 42:
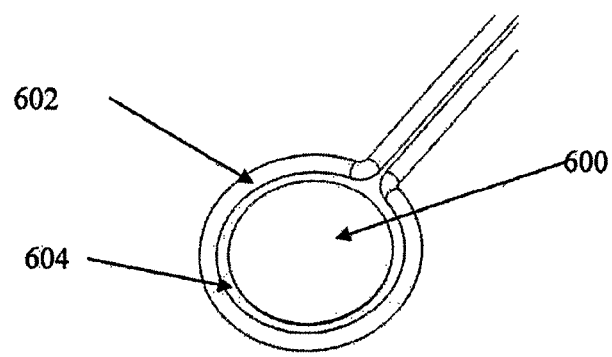
FIG. 42 illustrates an exemplary corneal implant positioning loop.

When the corneal implant is made from a hydrogel it is primarily liquid, and thus behaves in much the same way as a liquid. FIG. 42 illustrates handling tool 602 in the form of a loop in which fluid 604 and corneal implant 600 are constrained within the loop. When implant 600 is constrained in this manner within the loop, the implant can be moved from one location to another by grasping the handle connected to the loop. In some embodiments the implant is first picked up with a loop and is then deposited from within the loop into the recess in the minimal body.

Figure 43:
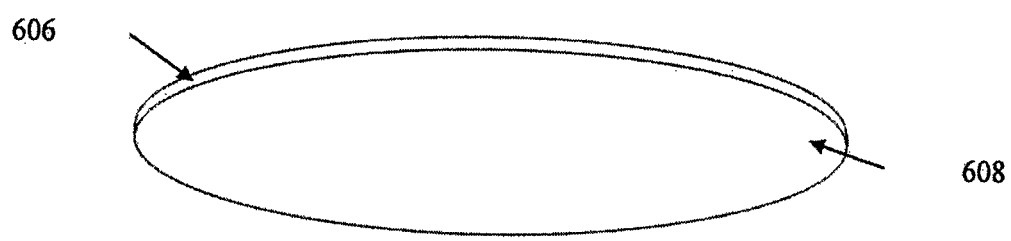
FIG. 43 illustrates an exemplary corneal implant.

There are several benefits for constraining the corneal implant within a droplet of fluid as is done in the embodiment in FIG. 42. First, forces acting on the implant are radial and maintain the implant in a substantially non-deformed configuration. Second, as shown in FIG. 43, for some corneal implants the radial surface area 606 is sufficiently less than a bottom surface (e.g., posterior surface) area 608 of the implant so that the bottom surface will preferentially adhere to another surface (e.g., corneal tissue) when the bottom surface is placed against the other surface. In some specific embodiments the corneal implant is a corneal inlay with a diameter of about 2 mm and an edge thickness of about 14 microns. In this specific embodiment the dimensions of this particular inlay dictate that the radial surface area is about $1/13^{th}$ of the bottom surface area.

Figures 44A, 44B, 44C, 44D:
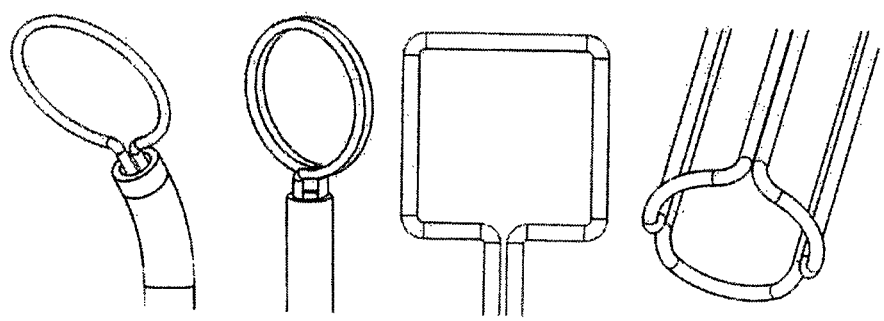
FIGS. 44A-44D illustrate exemplary loops.

While a round loop (as is shown in FIG. 42) may be preferential for drop formation, it is not necessary. Any number of wraps, angles, shapes, wires, sizes, or configurations may be used without departing from the scope of the present disclosure. FIGS. 44A-44D illustrate alternative configurations of loops. In FIG. 44A the loop is offset at an angle relative to the handle. FIG. 44B illustrates a loop in which the loop is a double loop of material. FIG. 44C illustrate the loop with a square configuration (but could be rectangular). FIG. 44D illustrates a loop in which the material forming the loop extends proximally to form the handle.

Figure 45:
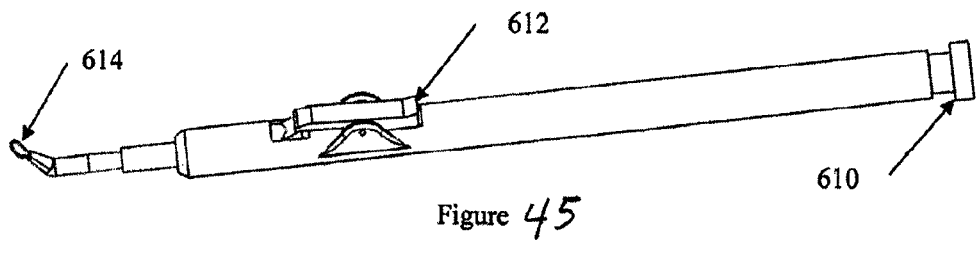
FIGS. 45-54 illustrate exemplary corneal implant positioning members that include loop structures.

FIG. 45 illustrates an embodiment of a handle designed to control loop 614 that is adapted to handle a corneal implant.

The corneal implant may be controlled with a volume of fluid held within loop 614. This handle allows the user to easily control the volume of fluid within the loop. In the embodiment shown in FIG. 45, there are two separate buttons 610 and 612. One of the buttons will cock a spring connected to a plunger, and the other button will release the spring. Both buttons will hold their position after release, preventing the user from having to hold a button in place while attempting to position the corneal implant.

Figure 46A:
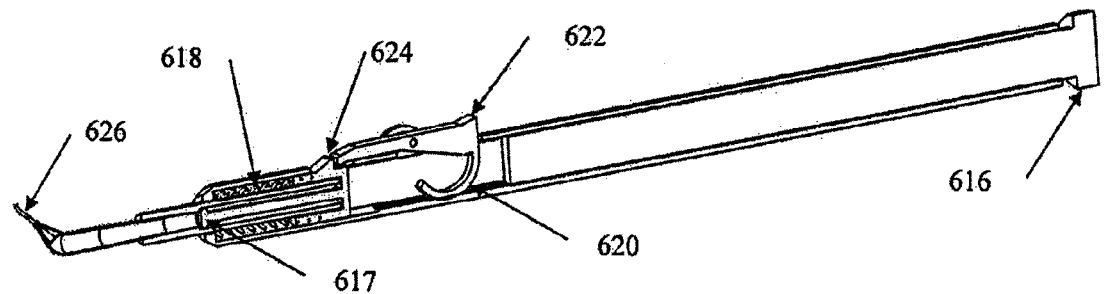
Figure 46B:
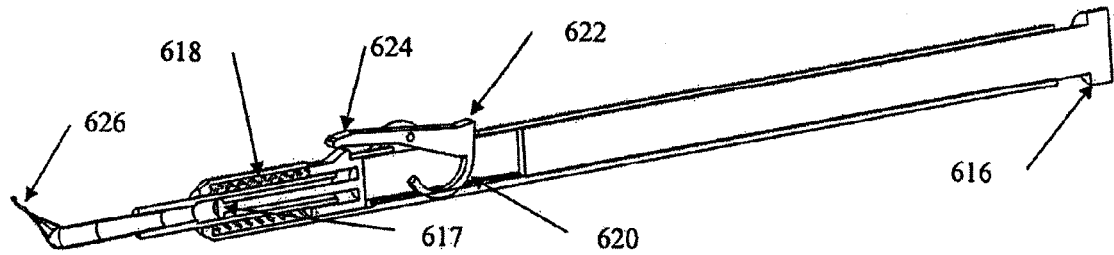

FIGS. 46a and 46b illustrate an exemplary embodiment of this dual actuator design, but other configurations of buttons can be used without departing from the scope of the present disclosure. When button 616 is depressed, spring 618 is cocked and spring 620 causes button 622 to engage latch 624. Button 616 is connected to plunger 617 such that it is pushed toward loop 626 when cocked. The device is now ready to pick up a corneal implant.

Once the loop is positioned on the cornea (with an implant within the loop), button 622 is pressed, latch 624 releases spring 618, which forces plunger 621 back away from loop 626. This causes air to move over the loop, sucking off excess fluid surrounding the corneal implant. To ensure the implant is released from the loop, plunger 621 is adapted to suck up an excess of fluid that is more than is be required to hold the implant within the loop.

The loop may be attached to any number of handle configurations to better allow for control of the corneal implant. For example, a handle that is adapted for precise control of the amount of fluid held within the loop is beneficial for several reasons. The amount of fluid within the loop will provide the user control of the corneal implant. To place the corneal implant onto a surface, such as the cornea, the user can hold a larger drop close to the surface and allow the fluid, along with the implant, to wick onto the surface, or the user can pull the fluid away from the loop until there is no longer enough fluid to create the needed surface tension, causing the implant to preferentially bind itself onto the corneal surface. If desired, the implant can be picked up by flooding the area with fluid, causing the implant to float to the top where it can be recaptured within the loop. Being able to remove excess fluid during the procedure is beneficial in that it takes less time for the surface of the cornea to dry. Once the implant has been placed onto the cornea, it is desirable to dry out the surface of the cornea to prevent the implant from moving for the duration of the procedure. The eye is particularly sensitive, and it is desirable to perform this procedure as quickly as possible. If excess fluid is minimized, the surface will dry quicker, and the procedure time will be minimized.

Figure 47:
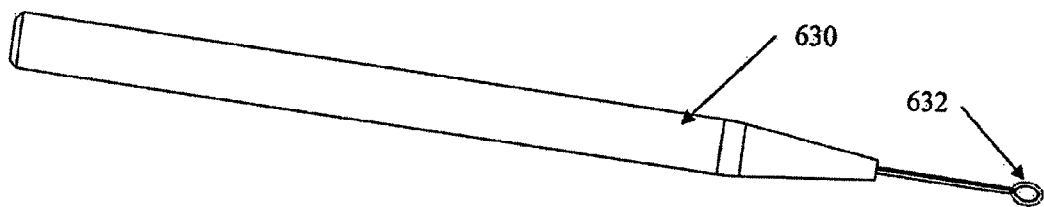

FIG. 47 illustrates an additional exemplary handle 630 coupled to loop 632. Loop 632, with fluid therein, is adapted to maintain a corneal implant therein. The control of the fluid within the loop may be achieved in a variety of suitable ways. In several of the following examples, the loop is placed at the end of a luer dispensing needle. However, any configuration placing the loop within a controlled fluid pathway may be used.

Figure 48:
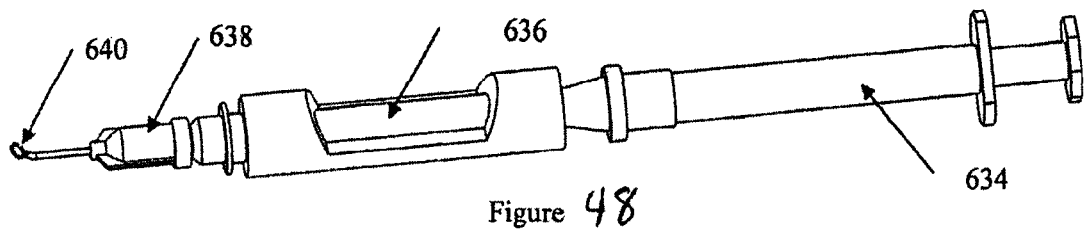

FIG. 48 shows an example of system that makes use of a compressible tubular element that forms control neck 636. The handle also includes luer 638. The reservoir is prefilled with fluid using syringe 634. When the user presses down on control neck 636, the volume inside of the handle decreases, forcing fluid out through the tip and into loop 640. When control neck 636 is released, a vacuum is created that sucks the fluid back into the reservoir.

Figure 49:
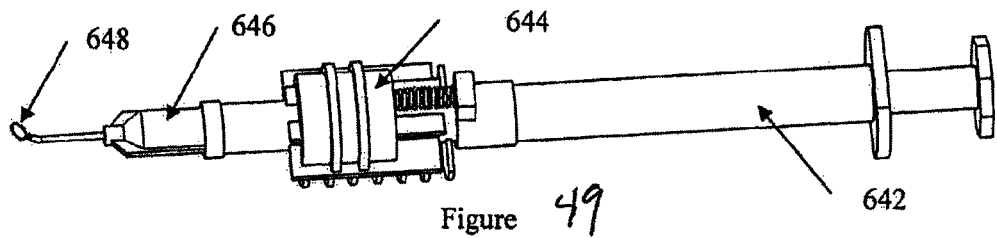

FIG. 49 shows a variation that works in much the same way as the embodiment in FIG. 48. Instead of the user pressing on a control neck manually, slide 644 is set at an intermediate position. This allows the user to release pressure on the internal tubing, resulting in a pressure differential to pull fluid in, or increase pressure to displace fluid, forcing it out of the tip. The spring forces the slide to return to the intermediary position upon release. The device includes syringe 642, luer 646, and loop 648.

Figure 50:
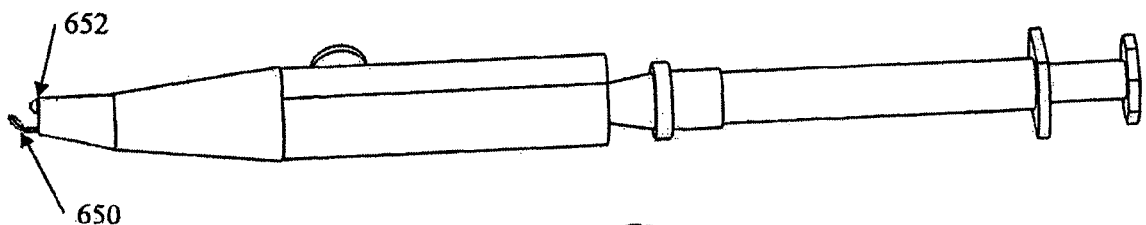

FIG. 50 is an embodiment in which lighting element 652 is added to the general handle design, which includes loop 650. The lighting element can be a LED at the distal end of the device, or it can be a fiber optic extending along the length of the device.

Figure 51:
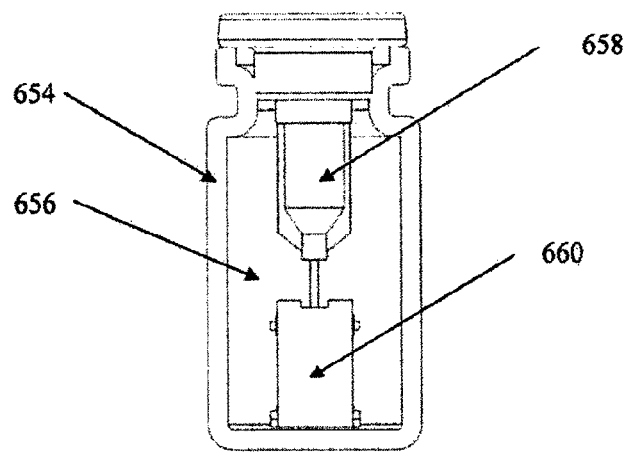

It may also be beneficial to be able to store a corneal implant within a loop. Some corneal implants are preferably placed on the cornea in a specific orientation and must be kept hydrated throughout shipment and storage. In these embodiments the implant can be packaged preloaded in the loop to preserve orientation, and within a package that preserves hydration. FIG. 51 shows an example of vial 654 that would house the packaged luer tip 658 while preserving hydration. Fluid 656 is also within vial 654. The implant is protected within protection package 660 within vial 654.

Figure 52:
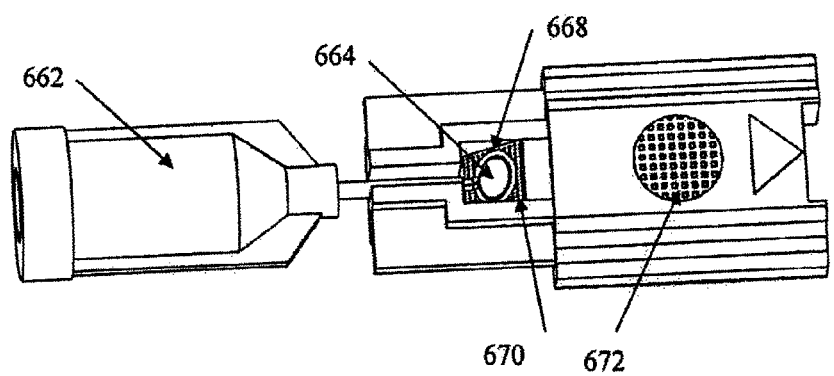

In some embodiments the preloaded loop is packaged within a small holder that allows fluid to flow therethrough to the implant to keep it hydrated. FIG. 52 shows an embodiment where cover 667 is slid back in the direction of the arrow to reveal loop 668 in which a preloaded inlay is disposed in its proper orientation. Mesh 672 on top and mesh 670 on bottom of implant 664 are adapted such that the implant preferentially adheres to the loop despite the larger surface area exposed to the mesh. The meshes with openings therethrough also allow for the implant to stay hydrated while packaged, and help excess fluid to drain off when the implant is removed from the hydration package. This embodiment also includes luer 665.

Figure 53:
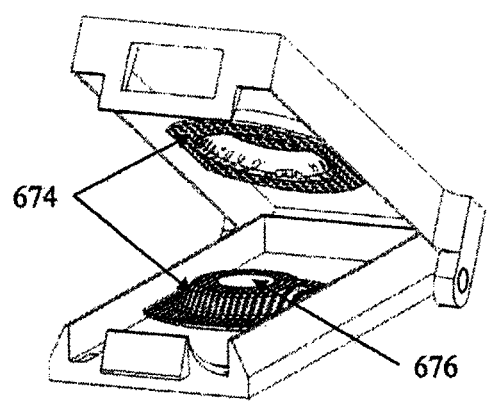

FIG. 53 shows a system in which the implant can be stored separately from the loop. Implant 676 can be easily removed from between meshes 674, which is the same mesh configuration shown in FIG. 52.

Figure 54:
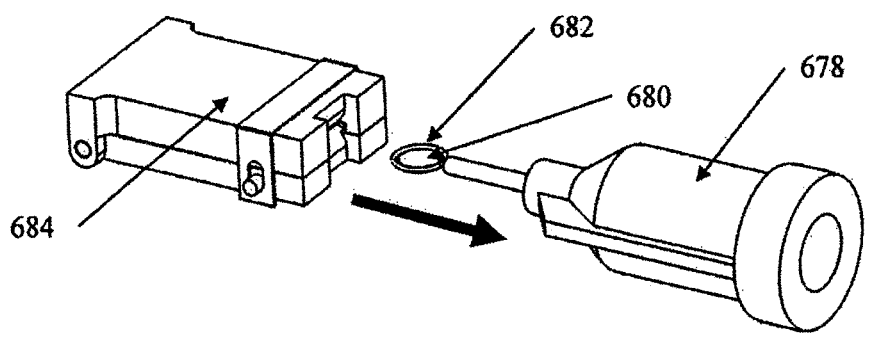

FIG. 54 illustrates a system in which preloaded loop 682 with implant 680 therein is placed within clamp 684, which is adapted to hold the implant in place during shipping and storage. At the time of use, a fluid control handle (not shown) is attached to luer 678. The entire assembly is then swiftly removed from the clamp with the implant retained in place within the loop.

Any of the loop devices described herein can also be used to position or move the corneal implant onto or from any type of surface. The loops can facilitate any kind of positioning or handling that might be needed. In some embodiments the loop is used to position a corneal implant onto a corneal surface. In some embodiments the loop is used to position a corneal implant onto a delivery device surface, wherein the delivery device is used to position the corneal implant into or onto the cornea. For example, the loop can be used to handle a corneal implant and position it into the recess of the minimal body described above. In some embodiments the loop is used to move the corneal implant from a storage or delivery device surface and onto another surface.

Embodiments herein describe both a moderate body and a minimal body. In some embodiments, however, the apparatus or its method of use need not include the minimal body. Without the minimal body, the corneal implant is not positioned within a corneal nest defined by the moderate and minimal bodies. The implant therefore need not be packaged with the moderate body. For example, it can be packaged in a separate packaging. In these embodiments the moderate body can utilize its preferential adhesion for the implant as set forth above to retrieve, or pick up, the corneal implant from its packaging. This can eliminate restrictions on how the corneal implant needs to be packaged. For example, the implant can be stored in a vial, free-floating in a storage medium. When the implant is ready to be positioned on the corneal tissue, the moderate body, which can be coupled to a handle, is positioned adjacent the implant in its storage medium, such as by scooping up the corneal implant into a position adjacent the apertures therein. Due to its preferential adhesion adaptation, the corneal implant will preferentially adhere to the moderate body. Once it has adhered to the moderate body, the implant is ready to be deposited onto the cornea as set forth above by relying on the moderate body's adaptation to allow the implant to preferentially adhere to the corneal tissue rather than the moderate body.

The invention claimed is:

1. A corneal implant applicator apparatus, comprising
an implant applicator with at least one applicator opening therethrough; and
an implant support with at least one support opening therethrough, wherein the implant applicator and implant support are disposed relative to one another to form an implant nest that is adapted to house a corneal implant;
wherein the at least applicator opening and the at least one support opening are adapted such that forces between the corneal implant and a liquid disposed in the at least one applicator opening are greater than forces between the corneal implant and a liquid disposed in the at least one support opening, wherein the greater forces provide the applicator with a greater affinity for the corneal implant than the support.

2. The apparatus of claim 1 wherein the at least one applicator opening are adapted to provide the applicator with less of an affinity for the corneal implant than a corneal surface.

3. The apparatus of claim 1 wherein the number of applicator openings is greater than the number of support openings.

4. The apparatus of claim 3 wherein the number of applicator openings that overlap the corneal implant when positioned in the implant nest is greater than the number of support openings that overlap the corneal implant.

5. The apparatus of claim 1 wherein the size of the at least one applicator opening is smaller than the size of the at least one support opening.

6. The apparatus of claim 1 wherein the implant applicator has a first surface through which the at least one applicator opening passes, wherein the first surface is flat.

7. The apparatus of claim 1 wherein the implant support has a first surface through which the at least one support opening passes, wherein the first surface is flat.

8. The apparatus of claim 1 wherein a ratio of the sum of the perimeters of the at least one applicator openings to the sum of the areas of the at least one applicator openings is greater than a ratio of the sum of the perimeters of the at least one support openings to the sum of the areas of the at least one support openings, and wherein the greater ratio provides the applicator with a higher affinity for a corneal implant than the support.

9. The apparatus of claim 1 wherein the at least one applicator opening and the at least one support opening have hexagonal configurations.

10. The apparatus of claim 1 wherein the implant applicator has a plurality of applicator openings therethrough and the implant support has a plurality of support openings therethrough, wherein the plurality of applicator openings are smaller than the plurality of support openings.

11. The apparatus of claim 1 wherein the implant applicator has a plurality of applicator openings therethrough and the implant support has a plurality of support openings therethrough, and wherein a number of the plurality of applicator openings that overlap the corneal implant when the corneal implant is disposed in the nest is greater than a number of the plurality of support openings that overlap the corneal implant.

12. The apparatus of claim 1 wherein the corneal implant is made from a hydrophilic material.

13. The apparatus of claim 1 wherein the implant applicator has a plurality of openings therethrough, and the implant support has a plurality of openings therethrough, and wherein the arrangement of the plurality of applicator openings provides the applicator with a higher affinity for the corneal implant than the support.

* * * * *